(12) United States Patent
Tang et al.

(10) Patent No.: US 12,377,177 B2
(45) Date of Patent: Aug. 5, 2025

(54) RADIONUCLIDE LABELED POLYPEPTIDE CONJUGATES AND USES THEREOF

(71) Applicant: TIANJIN CONJUSTAR BIOLOGICS CO., LTD., Tianjin (CN)

(72) Inventors: Shuyi Tang, Tianjin (CN); Cheng Xie, Tianjin (CN); Zhiping Cui, Tianjin (CN)

(73) Assignee: TIANJIN CONJUSTAR BIOLOGICS CO., LTD., Tianjin (CN)

( * ) Notice: Subject to any disclaimer, the term of this patent is extended or adjusted under 35 U.S.C. 154(b) by 0 days.

(21) Appl. No.: 18/646,785

(22) Filed: Apr. 26, 2024

(65) Prior Publication Data

US 2024/0366811 A1    Nov. 7, 2024

(30) Foreign Application Priority Data

Apr. 28, 2023 (CN) .......................... 202310479452.1
Jun. 13, 2023 (CN) .......................... 202310701839.7
Nov. 16, 2023 (CN) .......................... 202311531509.4

(51) Int. Cl.
   *A61K 51/08*    (2006.01)

(52) U.S. Cl.
   CPC ........ *A61K 51/088* (2013.01); *A61K 2123/00* (2013.01)

(58) Field of Classification Search
   CPC .......................... A61K 51/088; A61K 2123/00
   USPC .......................................................... 424/1.69
   See application file for complete search history.

(56) References Cited

U.S. PATENT DOCUMENTS

2019/0389906 A1* 12/2019 Beswick ................ A61K 38/10

FOREIGN PATENT DOCUMENTS

| CA | 3233035 A1 * | 4/2023 | ............. A61K 38/03 |
|---|---|---|---|
| CN | 102600489 A | 7/2012 | |
| CN | 104610431 A | 5/2015 | |
| CN | 115286693 A | 11/2022 | |
| CN | 115651063 A | 1/2023 | |
| WO | WO-2022253051 A1 * | 12/2022 | |
| WO | 2023020485 A1 | 2/2023 | |
| WO | 2023051396 A1 | 4/2023 | |

OTHER PUBLICATIONS

Price et al. Chem. Soc. Rev. 2014, 43, 260-290. (Year: 2014).*
Mudd et al. J. Med. Chem. 2022, 65, 14337-14347. (Year: 2022).*
Damalanka et al. J. Med. Chem. 2021, 64, 18158-18174. (Year: 2021).*

* cited by examiner

*Primary Examiner* — Michael G. Hartley
*Assistant Examiner* — Sean R Donohue
(74) *Attorney, Agent, or Firm* — Bayramoglu Law Offices LLC

(57) ABSTRACT

The present disclosure relates to a radioactive polypeptide conjugate drug and for use thereof in nuclear medicine as a tracer, an imaging agent, and for treating various disease states associated with tumors is provided.

3 Claims, No Drawings

RADIONUCLIDE LABELED POLYPEPTIDE CONJUGATES AND USES THEREOF

CROSS REFERENCE TO THE RELATED APPLICATIONS

This application claims priority to Chinese Patent Application No. 202310479452.1 filed on Apr. 28, 2023, Chinese Patent Application No. 202310701839.7 filed on Jun. 13, 2023, and Chinese Patent Application No. 202311531509.4 filed on Nov. 16, 2023, the entire contents of which are incorporated herein by reference.

TECHNICAL FIELD

The present disclosure relates to the technical field of biomedicine, and in particular to a therapeutic radioactive polypeptide drug conjugate.

BACKGROUND

RDC (radionuclide drug conjugate) is designed to reduce damage to normal tissues by attaching radionuclides to targeting agents to achieve precise irradiation of tumors. The biggest difference with other types of drug conjugates is that the payload of RDC is no longer a toxic molecule, but a radionuclide; the radionuclide therein can play a role in imaging diagnosis or killing tumors, and the conjugated targeting agent plays a role in precisely targeting tumors. Therefore, RDC can be used for both patient treatment and diagnostic imaging.

Radionuclides are atoms with too much energy to spontaneously emit particles or rays and release energy for diagnostic or therapeutic purposes, but their low stability, uncontrollability, and non-target site toxicity limit their use in medicine. Radionuclides are chelated with a chelator as payload and then conjugated with peptides through a linker to form polypeptide conjugated radionuclides, which guide the precise targeting of radionuclides, combined with the advantages of better tissue penetration and low immunogenicity of peptides, which can achieve ideal drug delivery in vivo, reduce toxicity and increase curative effect.

SUMMARY

The present disclosure provides a radioactive drug conjugate including a polypeptide fragment and a chelating group residue, and a linking group. Wherein the chelating group residue is connected to the polypeptide fragment through a chemical reaction between the linking group and the terminal amino group of the polypeptide, wherein the radioactive drug conjugate optionally includes 0-10 albumin binding fragments, wherein the polypeptide fragment has the following structure of formula (I-1) or (I-2):

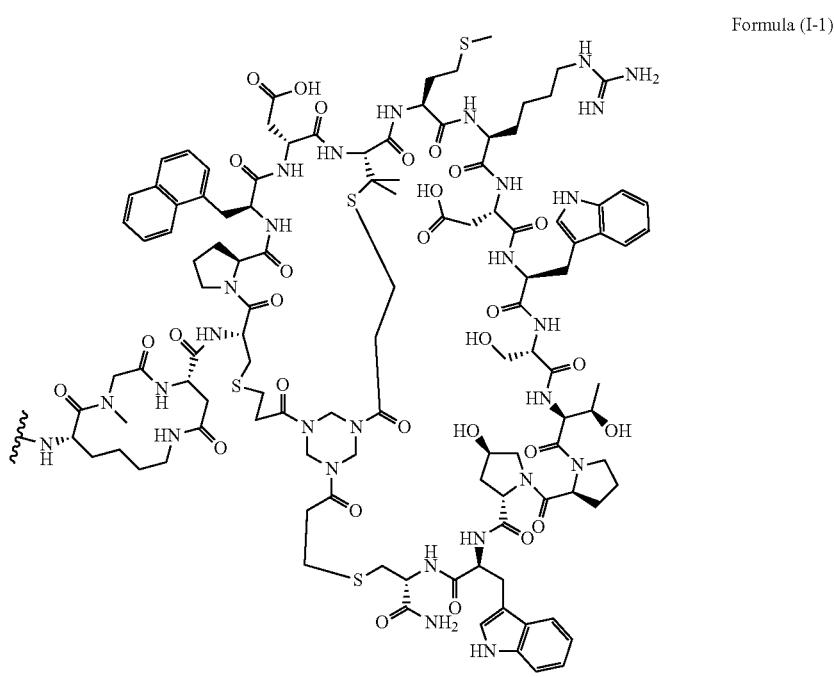

Formula (I-1)

-continued

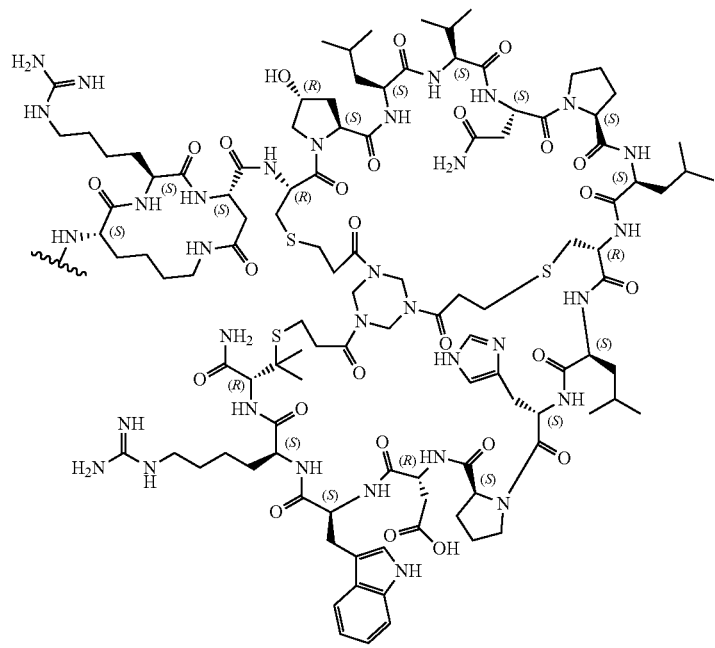

Formula (I-2)

The present disclosure provides a radioactive drug conjugate having the following structure of Formula (II):

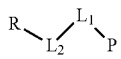

(II)

wherein $L_1$ represents absence or 1 to 100 amino acid residues, and any amino acid residue may optionally be inserted by 0 to 100 PEG groups or 0 to 100 PEG groups can be incorporated into the side chain of any optional amino acid residue;

wherein $L_2$ represents $-L_a-L_b-L_c-$;
wherein the $L_a$ represents a group selected from a bond, $-NR^a(CH_2)_mC(=O)-$, $-C(=O)(CH_2)_mNR^a$;
wherein $L_b$ represents a bond, a diacid residue;
wherein $L_c$ represents a bond, a diamine residue;
wherein $R_a$ each independently represents H or $C_1$-$C_6$ alkyl;
wherein m represents an integer of 0 to 100;
wherein, R represents a chelating group residue;
wherein 0-10 albumin binding fragments may be optionally connected to the $L_1$, $L_2$, or R structure,
wherein P represents the following structure:

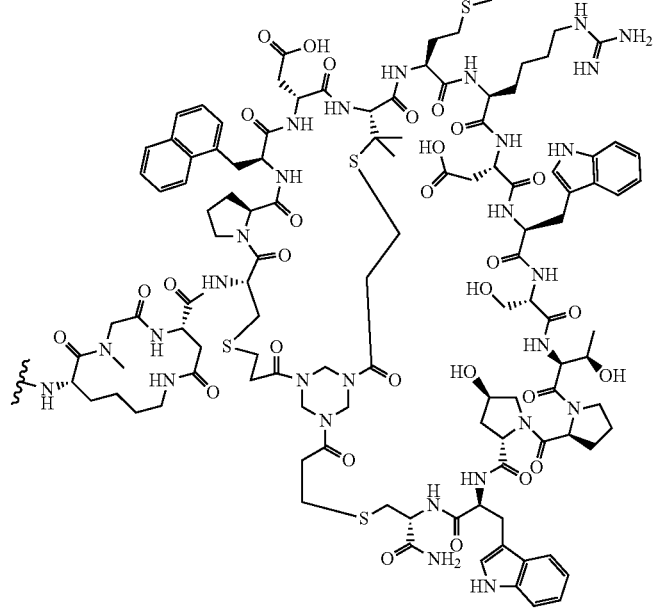

Formula (I-1)

-continued

Formula (I-2)

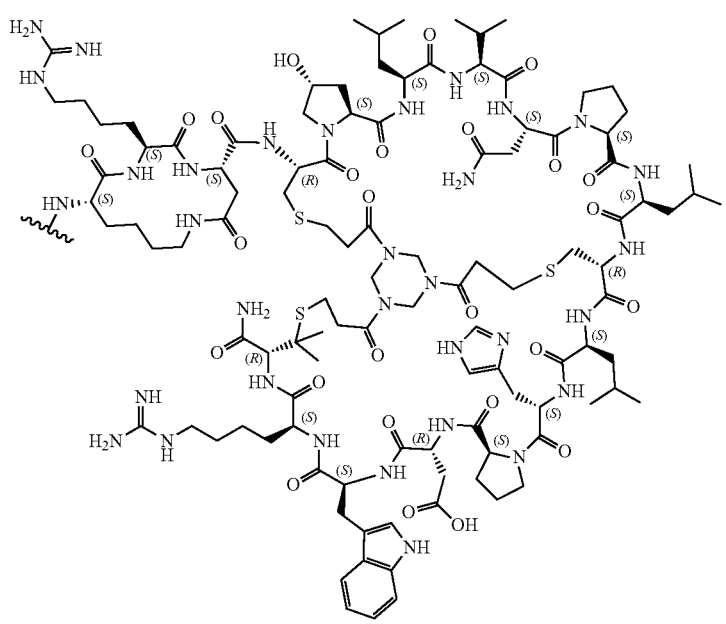

wherein, when $L_1$ is present, the wavy line represents the site binding to $L_1$;

wherein, when $L_1$ represents absence, the wavy line represents the site binding to $L_2$.

In one aspect of the disclosure, wherein $L_1$ represents absence.

In one aspect of the disclosure, wherein $L_1$ represents any one or any combination of natural or unnatural amino acids.

In one aspect of the disclosure, wherein $L_1$ represents any one or any combination of alanine, glycine, valine, lysine, phenylalanine, citrulline, leucine, aspartic acid, sarcosine, arginine, tyrosine, tryptophan, isoleucine, proline, cysteine, methionine, asparagine, glutamine, threonine, glutamic acid.

In one aspect of the disclosure, wherein $L_1$ represents the group: any one of -Val-Cit-, -Val-Ala-, -Gly-Gly-Phe-Gly-, Ala-Ala-Asn-, -Val-Lys-, -Phe-Lys-, -Phe-Cit-, -Phe-Arg-, -Phe-Ala-, -Ala-Lys-, -Leu-Cit-, -Ile-Cit-, -Trp-Cit-, -D-Phe-LPhe-Lys-, -Phe-Phe-Lys-, -D-Phe-Phe-Lys-, -Gly-Phe-Lys-, -Gly-Phe-Leu-Gly-, Ala-Leu-Ala-Leu or Sar or any combination thereof.

In one aspect of the present disclosure, wherein $L_1$ represents

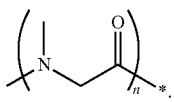

In one aspect of the present disclosure, wherein n represents an integer from 0 to 20, the asterisk represents the moiety attached to P.

In one aspect of the disclosure, wherein n represents 10.

In one aspect of the present disclosure, wherein $L_2$ represents -$L_a$-$L_b$-$L_c$-, wherein $L_a$ represents —$NR^a(CH_2)_mC(=O)$—, —$C(=O)(CH_2)_mNR^a$—, $L_b$ represents absence, and $L_c$ represents absence.

In one aspect of the disclosure, wherein $L_2$ represents -$L_a$-$L_b$-$L_c$-, wherein $L_a$ represents —$NR^a(CH_2)_mC(=O)$—, —$C(=O)(CH_2)_mNR^a$—, $L_b$ represents a diacid residue and $L_c$ represents a diamine residue.

In one aspect of the disclosure, wherein $L_a$ represents an oxalic acid residue, malonic acid residue, succinic acid residue, glutaric acid residue, and adipic acid residue.

In one aspect of the disclosure, wherein $L_b$ represents an ethylenediamine residue, a propylenediamine residue, a butylenediamine residue, a pentylenediamine residue, and a hexylenediamine residue.

In one aspect of the disclosure, wherein the albumin binding fragment is selected from any one or a combination of the following:

(i)

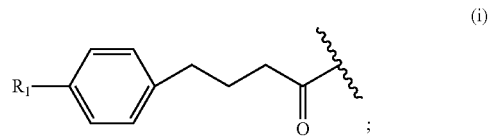

(ii)

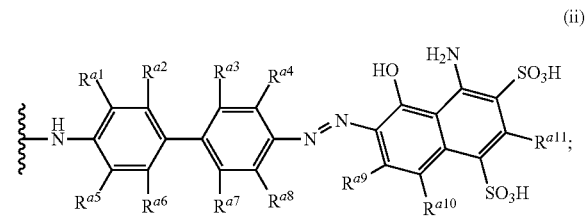

wherein $R_1$ represents H, halogen (fluorine, chlorine, bromine, iodine, preferably iodine);

wherein $R^{a1}$ to $R^{a11}$ each independently represents hydrogen, $C_1$-$C_6$ alkyl, $C_1$-$C_6$ alkoxy, halogen, cyano, nitro, amino, hydroxyl, and halogen;

wherein the albumin binding fragment is linked to the radioactive drug conjugate via $L_3$;

wherein $L_3$ represents —C(O)— or

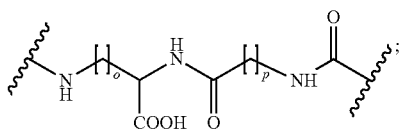

wherein o or p represents an integer selected from 1 to 10.

In addition, the present disclosure also provides a radioactive drug conjugate having the following structural formula (III):

Formula (III)

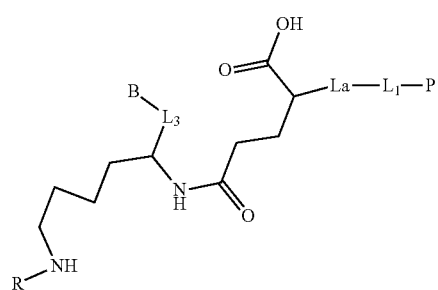

wherein $L_1$ represents a bond,

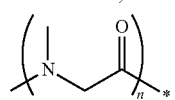

wherein the asterisk indicates the moiety attached to P and n represents an integer from 0 to 20;
wherein $L_a$ represents a bond, —C(=O)—(CH$_2$)$_m$—NH— or —NH—(CH$_2$)$_m$—C(=O)—;
wherein $L_3$ represents —C(O)— or

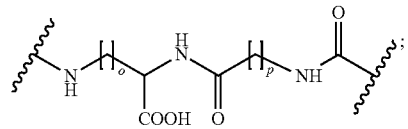

wherein B represents an albumin binding moiety selected from the following structures:

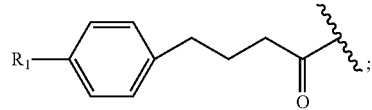
(i)

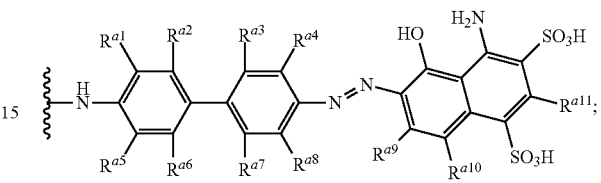
(ii)

wherein $R_1$ represents H, halogen (fluorine, chlorine, bromine, iodine, preferably iodine);
wherein $R^{a1}$ to $R^{a11}$ each independently represents hydrogen, $C_1$-$C_6$ alkyl, $C_1$-$C_6$ alkoxy, halogen, cyano, nitro, amino, hydroxyl, and halogen;
wherein m, n, o, p each independently represents an integer from 0 to 100; preferably from 0 to 50; 0-20; 0-10; 1-10;
wherein P represents the following group:

Formula (I-1)

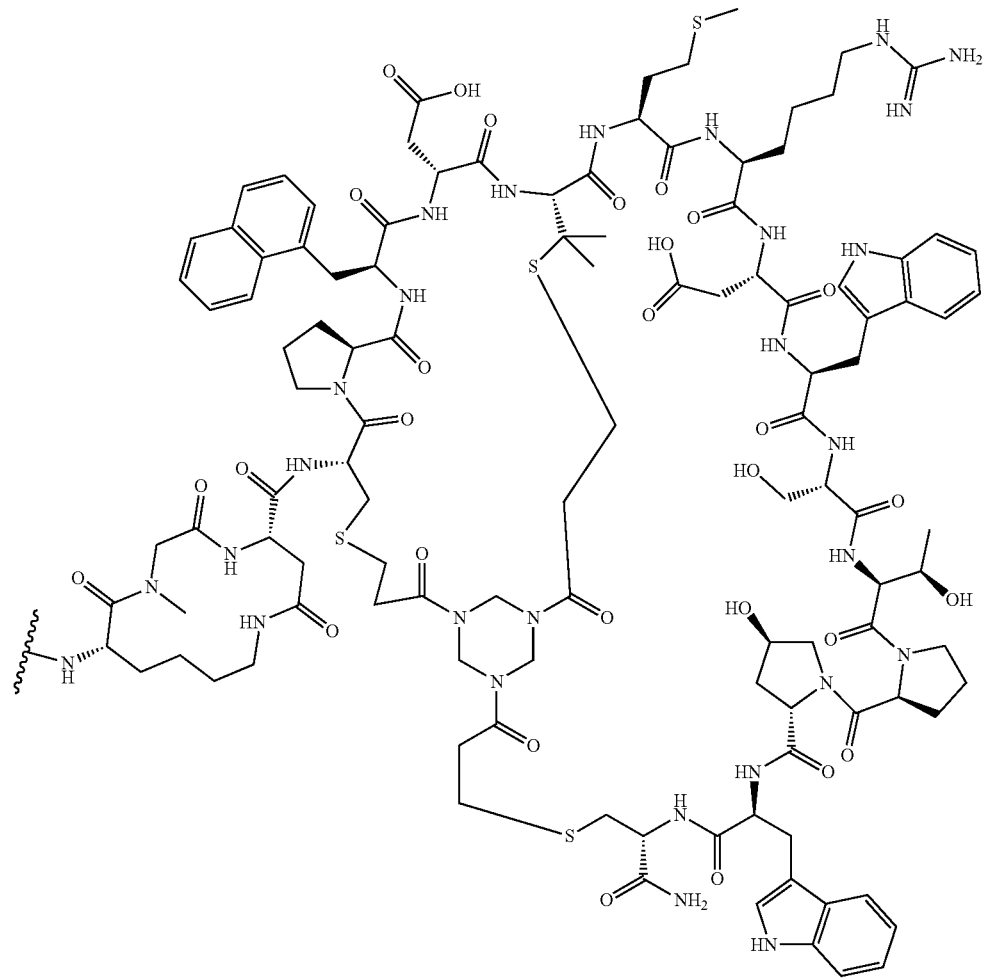

-continued

Formula (I-2)

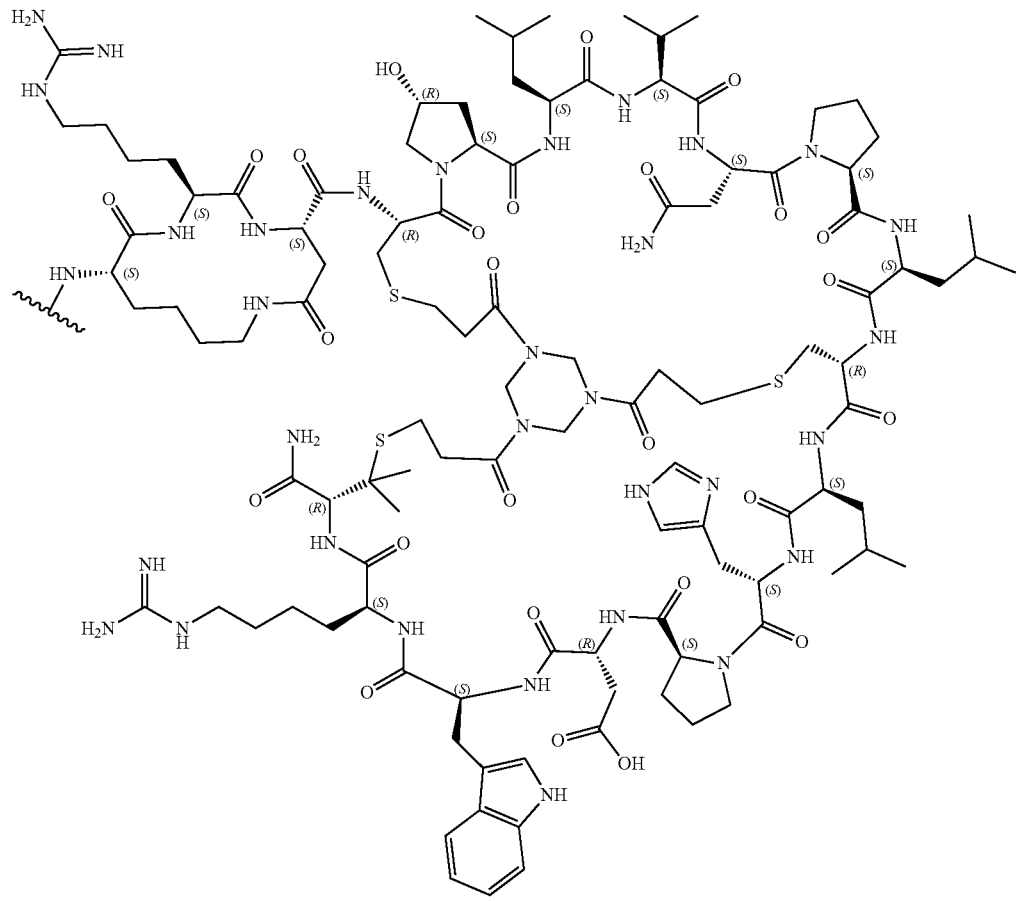

wherein R represents a chelating group residue.

The present disclosure provides a radioactive drug conjugate having the following structural formula (IV):

R-La-L₁-P    Formula (IV)

wherein L₁ represents a bond,

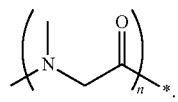

wherein the asterisk represents the moiety attached to P;

wherein $L_a$ represents a bond, —NH(CH$_2$)$_m$C(=O)—, —C(=O)—(CH$_2$)$_m$—N—;

wherein m, n represents an integer of 0 to 100; preferably from 0 to 50; 0-20; 0-10; 1-10;

wherein P represents the following group:

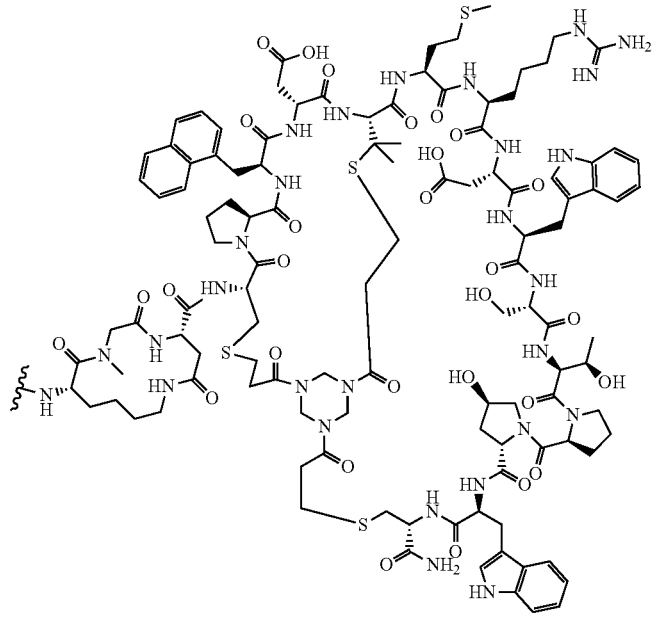

Formula (I-1)

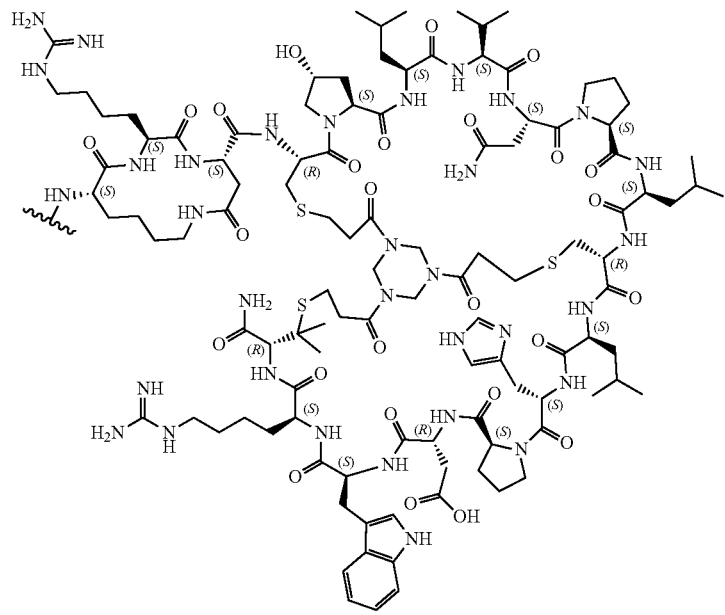

Formula (I-2)

wherein R represents a chelating group residue.

In one aspect of the disclosure, wherein the chelating group residue is selected from the group consisting of bis(carboxymethyl)-1,4,8,11-tetraazabicyclo[6.6.2]hexadecane (CBTE2a), cyclohexyl-1,2-diamine tetraacetic acid (CDTA), 4-(1,4,8,11-tetraazacyclotetradec-1-yl)-methylbenzoic acid (CPTA), N'-[5-[acetyl(hydroxy) amino]pentyl]-N-[5-[[4-[5-aminopentyl-(hydroxy) amino]-4-oxobutanoyl]amino]pentyl]-N-hydroxysuccinamide (DFO), 4,11-bis(carboxymethyl)-1,4,8,11-tetraazabicyclo[6.6.2] hexadecane (DO2A), 1,4,7,10-tetraazacyclododecane-N,N', N'',N'''-tetraacetic acid (DOTA), α-(2-carboxyethyl)-1,4,7, 10-tetraazacyclododecane-1,4,7,10-tetraacetic acid (DOTAGA), 1,4,7,10-azacyclododecane-N,N',N'',N'''-1,4, 7,10-tetra(methylene)phosphonic acid (DOTMP), N,N'-dipyridoxyethylenediamine-N,N'-diacetic acid-5,5''-bis (phosphate) (DPDP), diethylenetriamine N,N',N''-penta (methylene)phosphonic acid (DTMP), diethylenetriamine pentaacetic acid (DTPA), ethylenediamine-N,N'-tetraacetic acid (EDTA), ethylene glycol-0,0-bis(2-aminoethyl)-N,N,N'',N''-tetraacetic acid (EGTA), N,N-bis(hydroxybenzyl)-ethylenediamine-N,N''-diacetic acid (HBED), hydroxyethyl ethylenediamine triacetic acid (HEDTA), 1-(p-nitrobenzyl)-1,4,7,10-tetraazacyclodecane-4,7,10-triacetate (HP-DOA3), 6-hydrazino-N-methylpyridine-3-carboxamide (HYNIC), tetra 3-hydroxy-N-methyl-2-pyridone chelator (4-((4-(3-(bis (2-(3-hydroxy-1-methyl-2-oxo-1,2-dihydropyridine-4-carboxamido)ethyl) amino)-2-((bis(2-(3-hydroxy-1-methyl-2-oxo-1,2-dihydropyridine-4-carboxamido)ethyl)amino) methyl)propyl)phenyl)amino)-4-oxobutanoic acid) abbreviated as Me-3,2-HOPO, 1,4,7-triazacyclononane-1-succinic acid-4,7-diacetic acid (NODASA), 1-(1-carboxy-3-carboxypropyl)-4,7-(carboxy)-1,4,7-triazacyclononane (NODAGA), 1,4,7-triazacyclononane triacetic acid (NOTA), 4,11-bis(carboxymethyl)-1,4,8,11-tetraazabicyclo [6.6.2]hexadecane (TE2A), 1,4,8,11-tetraazacyclododecane-1,4,8,11-tetraacetic acid (TETA), tris(hydroxypyridinone) (THP), terpyridine-bis(methyleneamine tetraacetic acid (TMT), 1,4,7-triazacyclononane-1,4,7-tris[methylene (2-carboxyethyl)phosphinic acid](TRAP), 1,4,7,10-tetraaza-cyclo-tridecane-N,N',N'',N'''-tetraacetic acid (TRITA), 3-[[4,7-bis[[2-carboxyethyl(hydroxy)phosphoryl]methyl]-1, 4,7-triazacyclononan-1-yl]methyl-hydroxy-phosphoryl]propanoic acid and triethylenetetramine hexaacetic acid (TTHA), wherein one or more carboxyl groups of the chelating group are connected to the $L_a$ residue.

In one aspect of the disclosure, the chelating group is selected from the group consisting of:

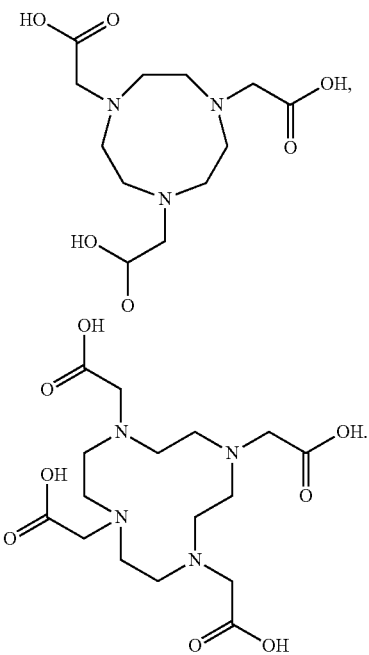

Wherein one carboxyl group of the chelating group is connected to a $L_a$ residue.

In one aspect of the disclosure, wherein the chelating group residue further includes a radioactive ion.

In particular, the present disclosure provides a radioactive drug conjugate having the following structure:

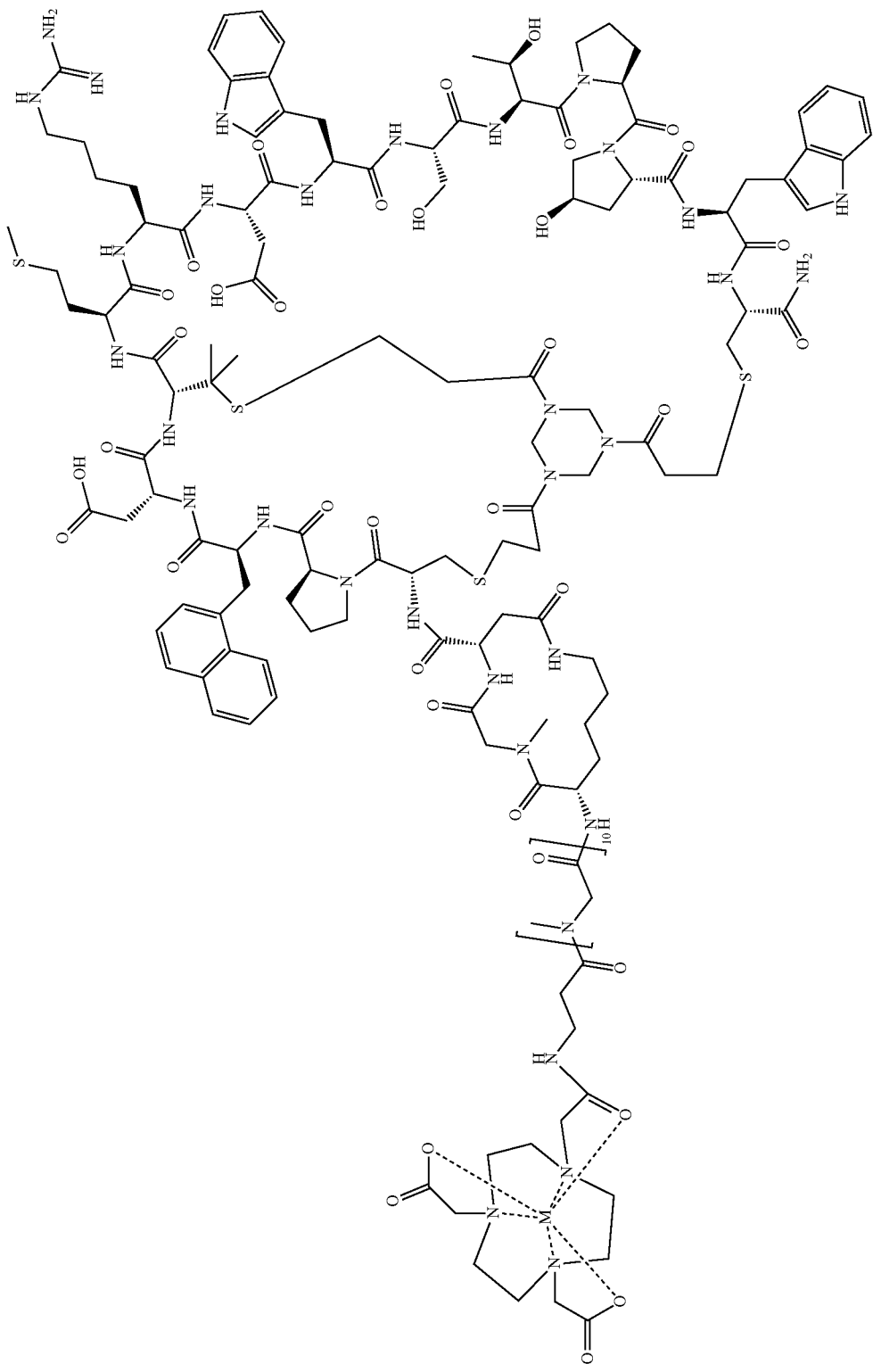

-continued
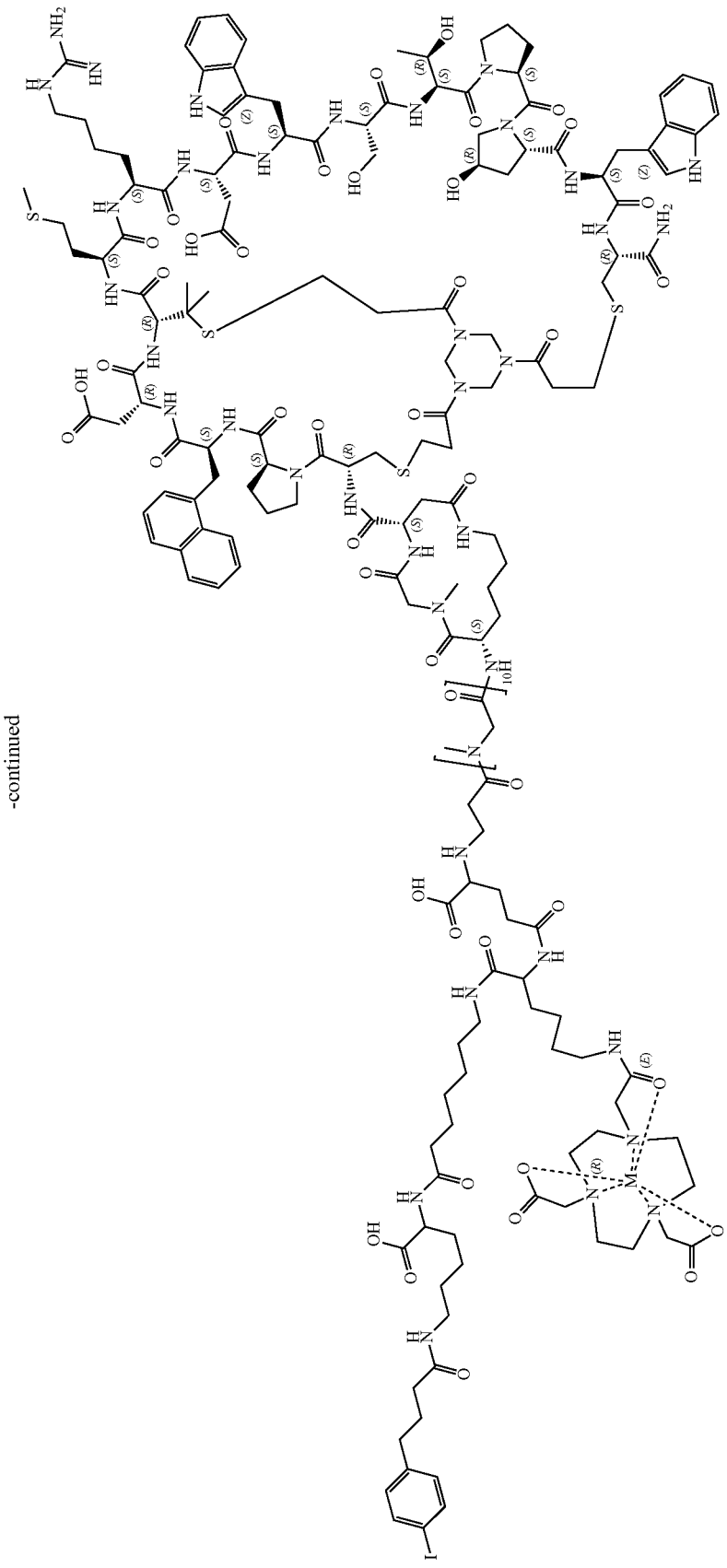

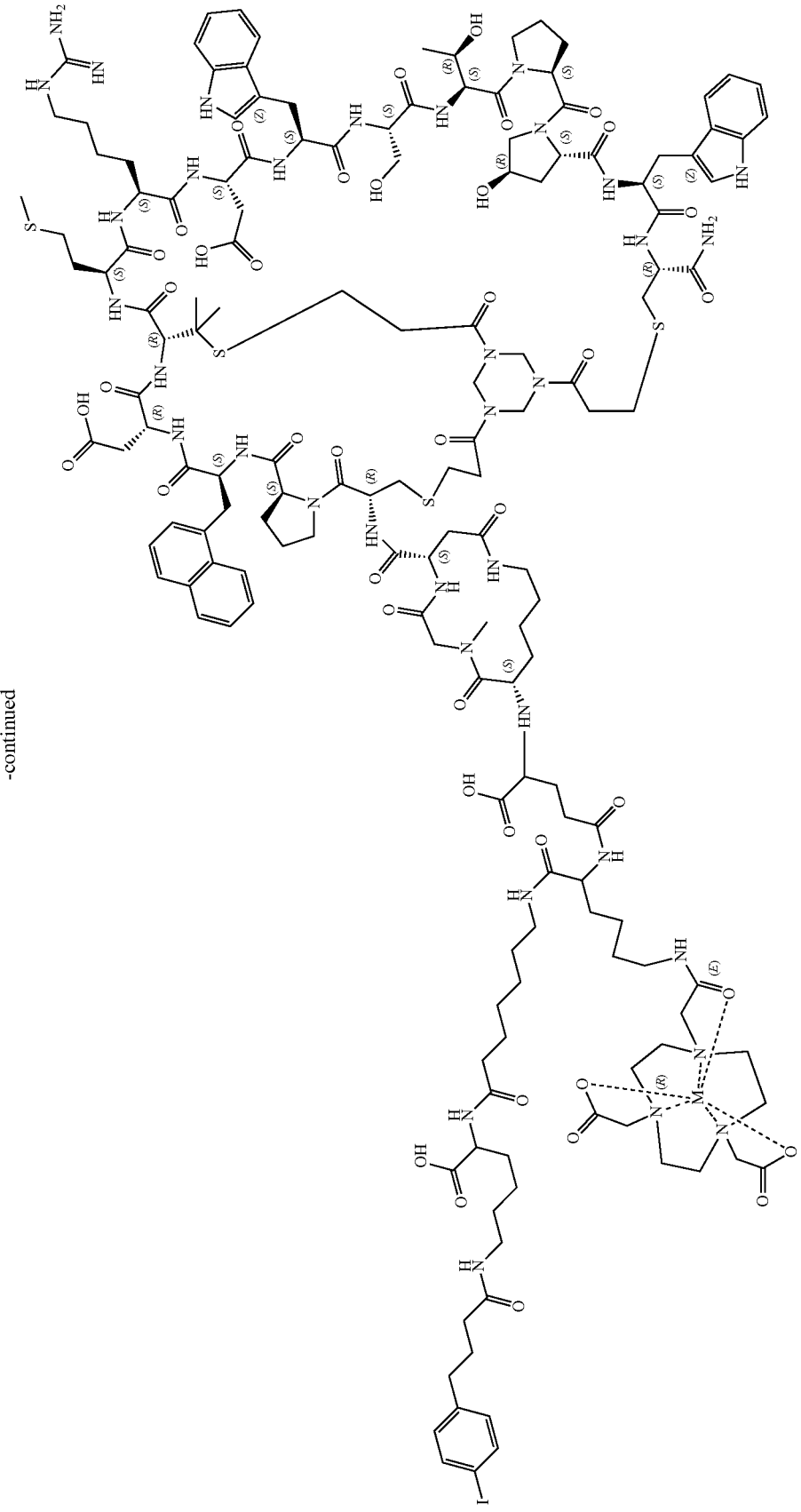

-continued
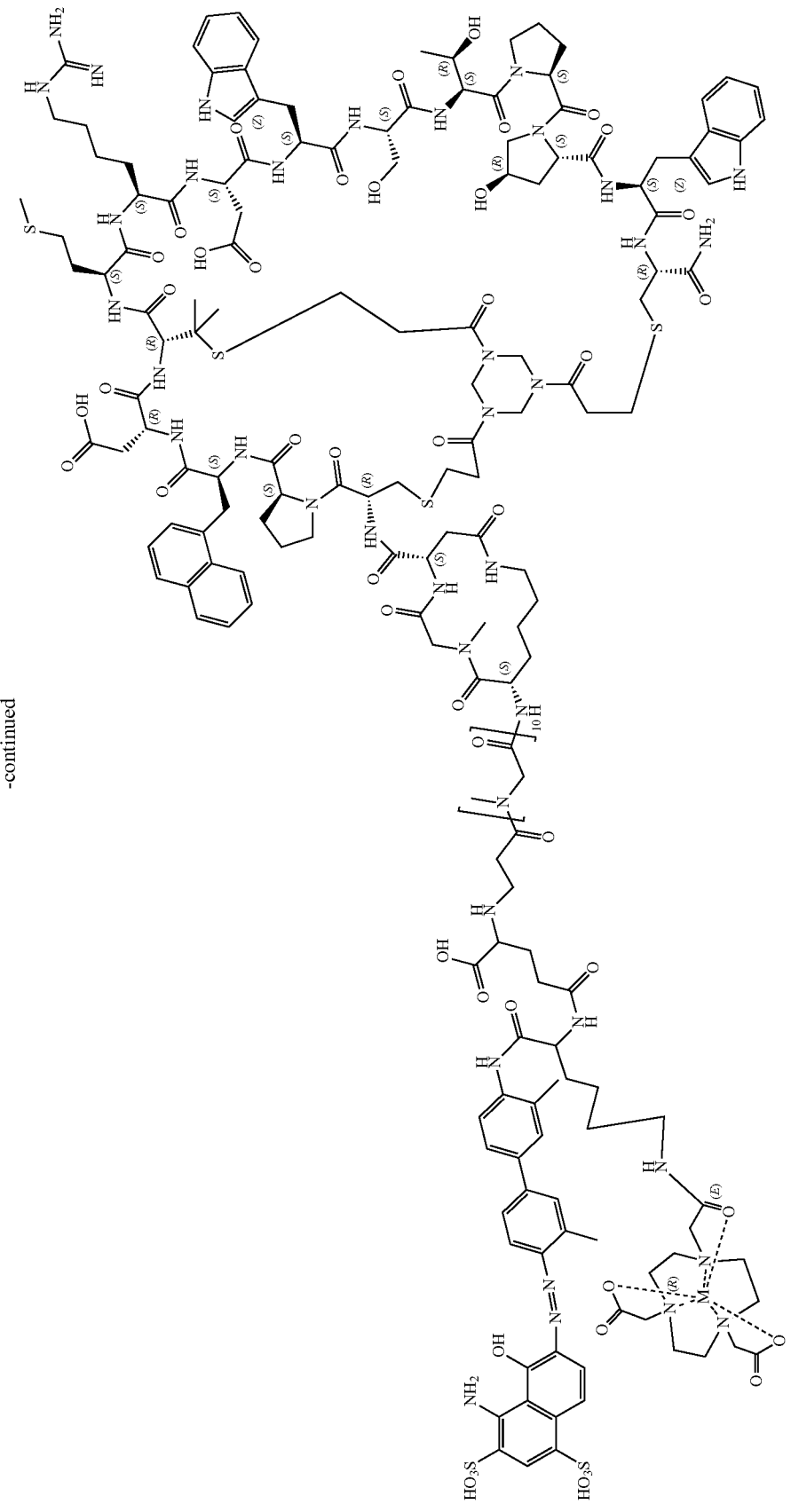

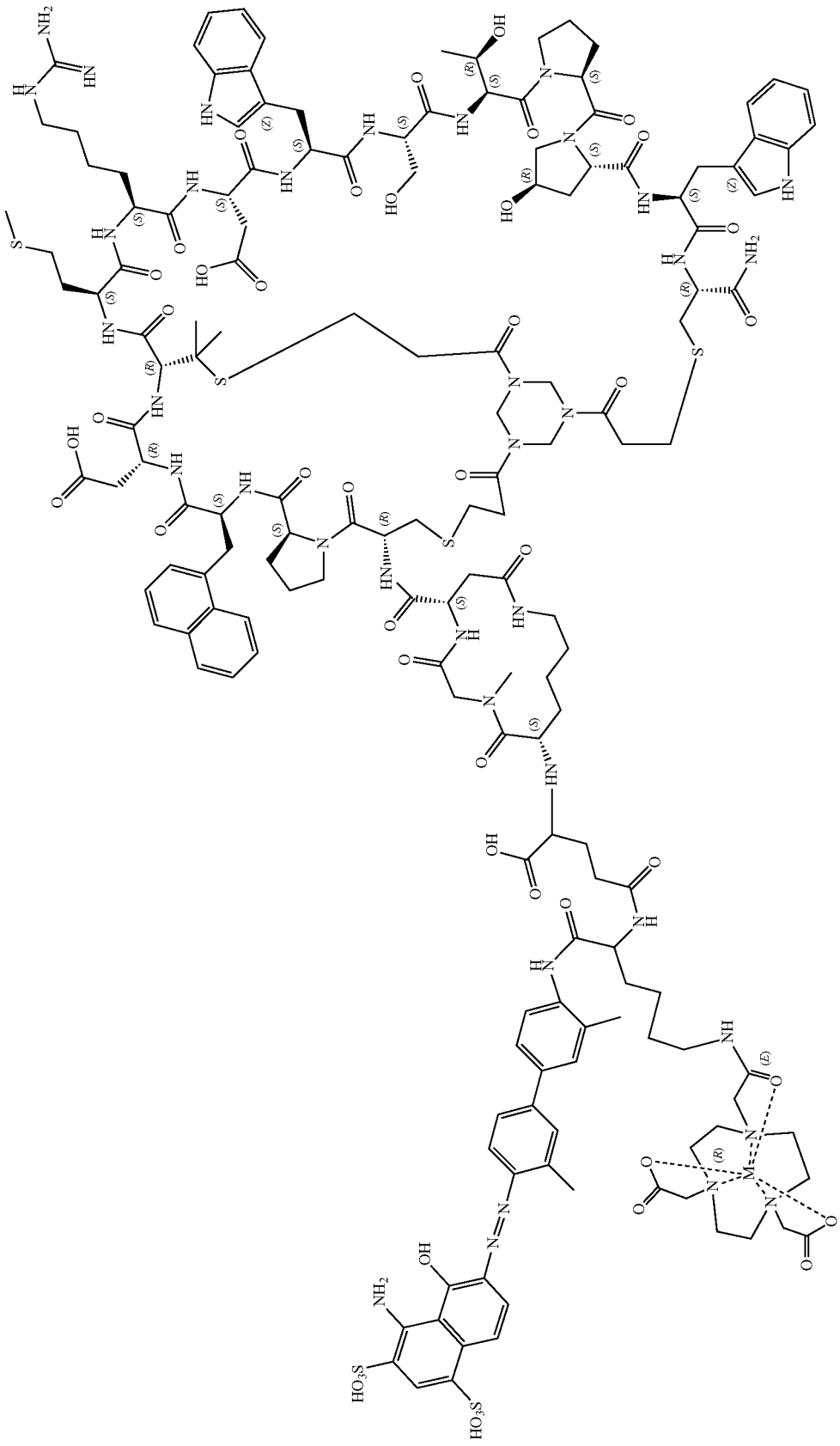

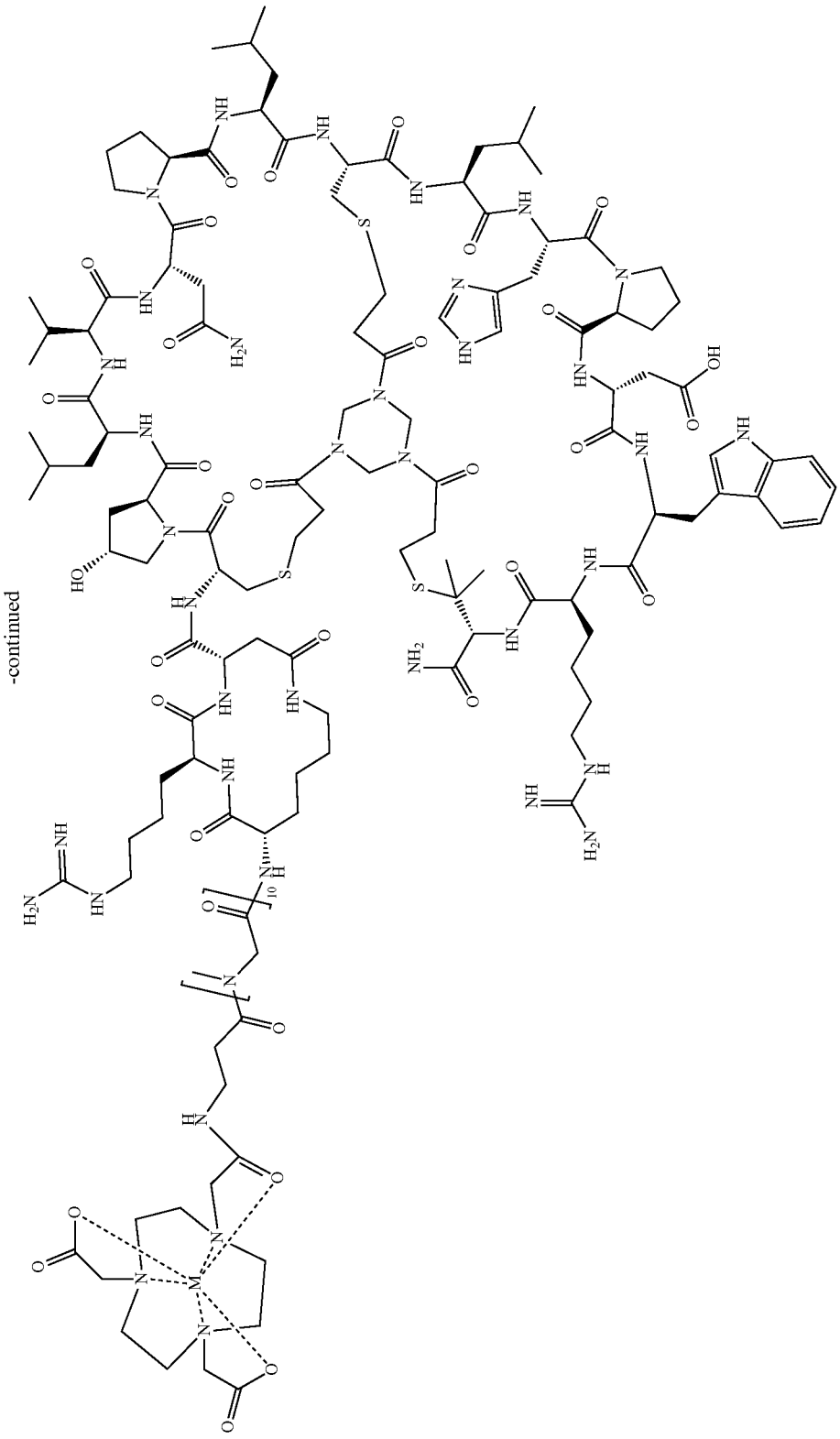

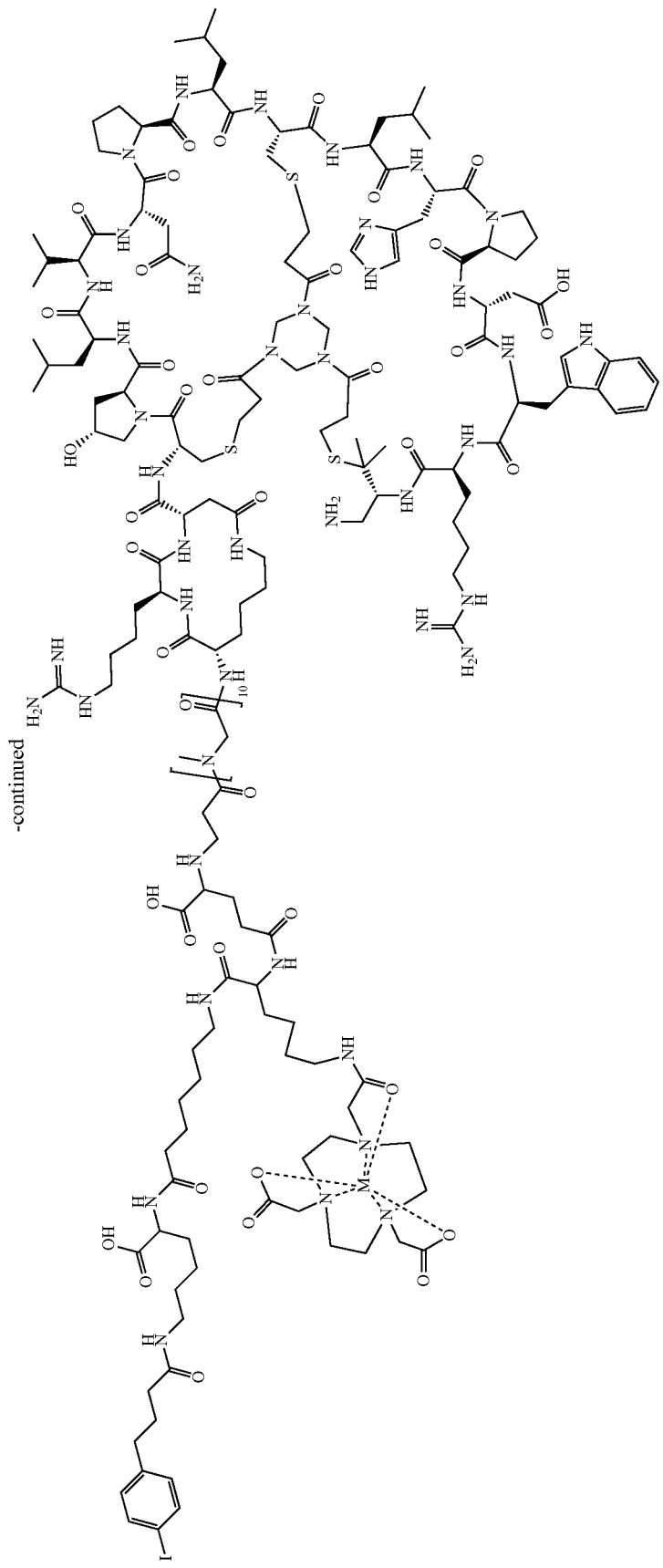

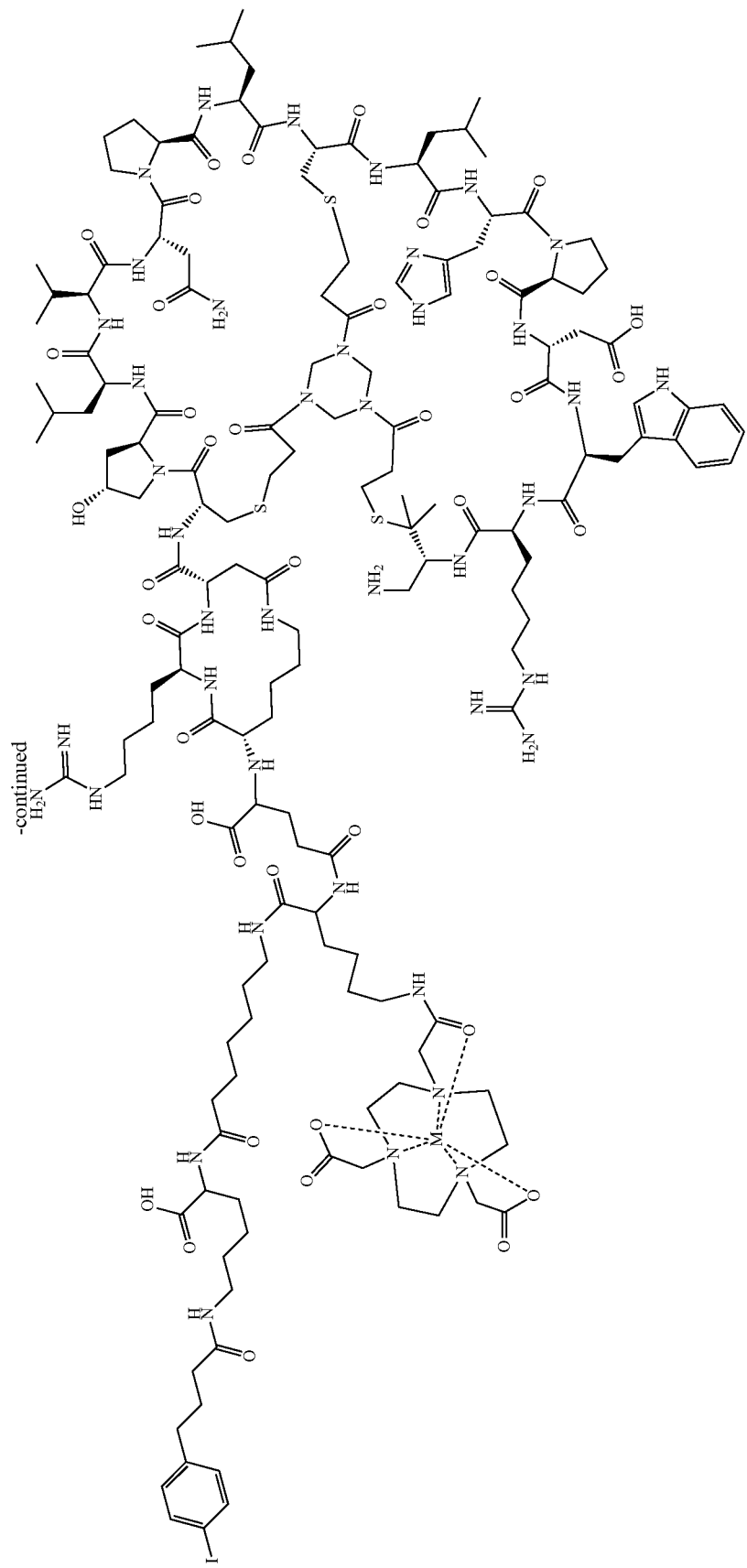

-continued
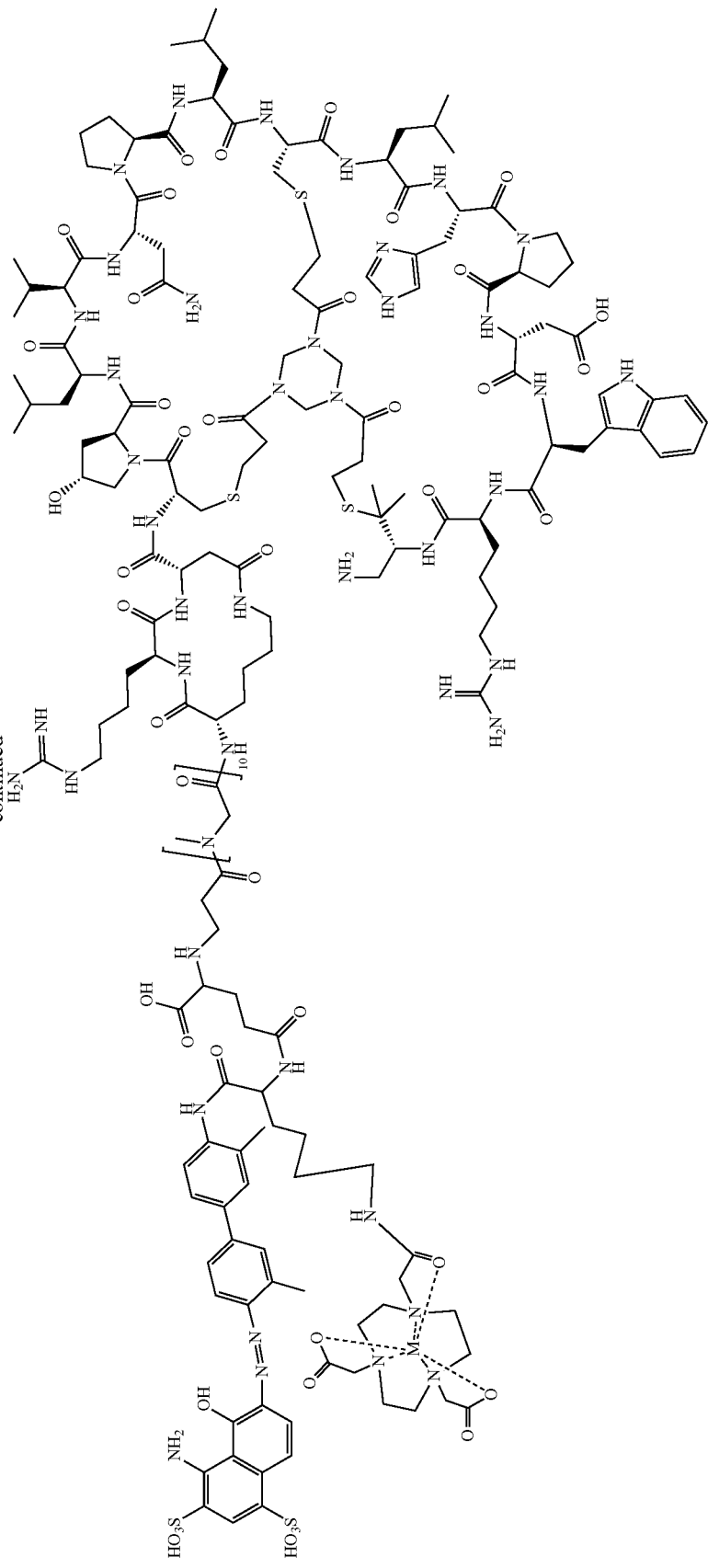

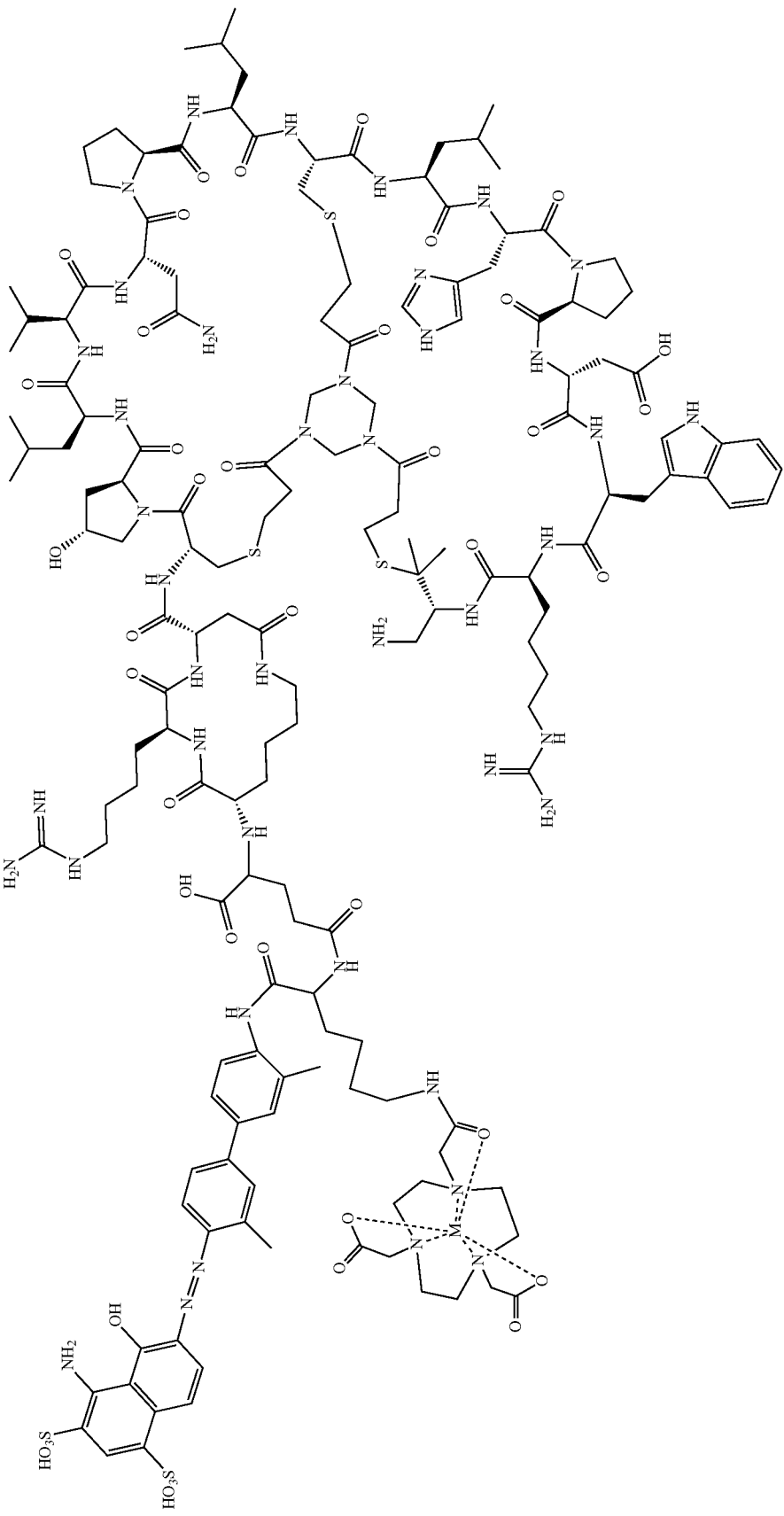

wherein M represents a radioactive ion.

In one aspect of the disclosure, wherein the chelating group residue includes a chelating radioactive ion selected from F, Br, I, Sc, Cu, Ga, Y, In, Lu, Tc, Sm, Sr, Ra, Tb, Ho, Lu, Re, Pb, Bi, Ac, Th, Zr, At or Er.

In one aspect of the disclosure, wherein the chelating radioactive ion is selected from $^{131}$I, $^{125}$I, $^{111}$In, $^{177}$Lu, $^{68}$Ga, $^{99}$Tc, $^{153}$Sm, $^{89}$Sr, $^{223}$Ra, $^{188}$Re, $^{90}$Y, $^{18}$F, $^{89}$Zr, $^{64}$Cu, $^{225}$Ac, $^{223}$Ra, $^{213}$Bi, $^{211}$At, $^{188}$Re, $^{77}$Br, $^{212}$Pb.

DETAILED DESCRIPTION OF THE EMBODIMENTS

Many other modifications, substitutions, and alterations are possible in light of the above teaching of the present disclosure without departing from the basic technical spirit of the present disclosure.

I. DEFINITION OF TERMS

The term "alkyl", by itself or as part of another substituent, means, unless otherwise stated, a straight (i.e. unbranched) or branched chain, or cyclic hydrocarbon radical, or combinations thereof, which may be saturated, mono- or polyunsaturated and may include di- or multivalent groups, having the number of carbon atoms designated (i.e. C1-C10 means one to ten carbon atoms). Examples of saturated hydrocarbon groups include but are not limited to, groups such as methyl, ethyl, n-propyl, isopropyl, n-butyl, t-butyl, isobutyl, sec-butyl, cyclohexyl, cyclohexylmethyl, cyclopropylmethyl, homologs and isomers such as n-pentyl, n-hexyl, n-heptyl, n-octyl, and the like. An unsaturated alkyl group is an alkyl group having one or more double or triple bonds. Examples of unsaturated alkyl groups include but are not limited to, ethenyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups defined as hydrocarbon groups are termed "homoalkyl". The alkyl group is optionally substituted with one or more halogen atoms.

The term "haloalkyl" refers to an alkyl group as defined above wherein one or more hydrogen atoms are replaced by a halogen atom.

The term "cycloalkyl" refers to a monocyclic or bicyclic saturated carbocyclic ring, each having from 3 to 10 carbon atoms. A "fused analog" of a cycloalkyl group refers to a monocyclic ring fused to an aryl or heteroaryl group, wherein the point of attachment is in the non-aromatic portion. Examples of cycloalkyl groups and fused analogs thereof include cyclopropyl, cyclobutyl, cyclopentyl, cyclohexyl, tetrahydronaphthyl, decahydronaphthyl, indanyl, and the like. The cycloalkyl is optionally substituted with one or more halogen atoms. Further, in the present invention, the term "cycloalkyl" includes bridged ring systems and spiro ring systems.

The use of the articles "a", "an" and "the" in the specification and claims are to be construed to cover both the singular and the plural unless otherwise indicated herein or clearly contradicted by context.

Unless otherwise indicated, for example, the terms "comprise", "have", "being of" (e.g. a complex "of a radionuclide and a cell-binding receptor organic moiety attached to a chelator") "including" and "containing" are to be interpreted as open-ended terms (i.e. "including, but not limited to,"). In addition, when "comprising" or another open-ended term is used in an embodiment, it is understood that the same embodiment may be more narrowly claimed using the intermediate term "consisting essentially of or the closed term" consisting of.

The term "about" or "proximately" herein has the following meaning: the following values may vary by ±20%, preferably ±10%, more preferably ±5%, even more preferably ±2%, even more preferably ±1%.

The term "about" or "proximately" herein has the following meaning: the following values may vary by ±20%, preferably ±10%, more preferably ±5%, even more preferably ±2%, even more preferably ±1%.

As used herein, the term "cancer" refers to a cell having the ability to grow autonomously, i.e. an abnormal state or condition characterized by rapidly proliferating cell growth. Hyperproliferative and neoplastic disease states may be classified as pathological, i.e. characterizing or constituting a disease state, or non-pathological, i.e. deviating from a normal state but not associated with a disease state. Unless otherwise indicated, the term includes all types of cancerous growths or oncogenic processes, metastatic tissues, or malignantly transformed cells, tissues, or organs, irrespective of histopathological type or invasive stage.

As used herein, the term "cancer" refers to a cell having the ability to grow autonomously, i.e. an abnormal state or condition characterized by rapidly proliferating cell growth. Hyperproliferative and neoplastic disease states may be classified as pathological, i.e. characterizing or constituting a disease state, or non-pathological, i.e. deviating from a normal state but not associated with a disease state. Unless otherwise indicated, the term includes all types of cancerous growths or oncogenic processes, metastatic tissues, or malignantly transformed cells, tissues, or organs, irrespective of histopathological type or invasive stage.

As used herein, the term numerical range, e.g. "an integer from 0 to 100", represents 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100.

As used herein, reference to a repeat unit does not mean that when the number of repeat units is 2 or more (≥2), e.g. when j is 2 or more (≥2) in the structure

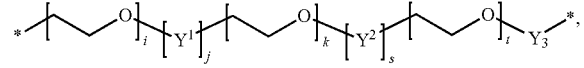

Y1 therein does not necessarily mean identical, i.e. the natural or unnatural amino acid residues from which Y1 represented by the repeat unit is selected may be identical, e.g. one Y1 is a glycine residue and the other Y1 is an alanine residue (to name but a non-exhaustive list).

II. EXAMPLES

The present disclosure is further illustrated with reference to the following examples. The description of specific exemplary embodiments of the disclosure is for purposes of illustration and illustration. It is not intended to limit the disclosure to the precise form disclosed, and obviously, many modifications and variations are possible in light of the teaching of the present disclosure. The exemplary embodiments were chosen and described in order to explain the specific principles of the disclosure and its practical application to enable one skilled in the art to make and use the disclosure in various exemplary embodiments and with various alternatives and modifications.

The experimental methods used in the following examples are conventional unless otherwise specified. Materials, reagents, and the like used in the examples are commercially available unless otherwise specified.

Example 1

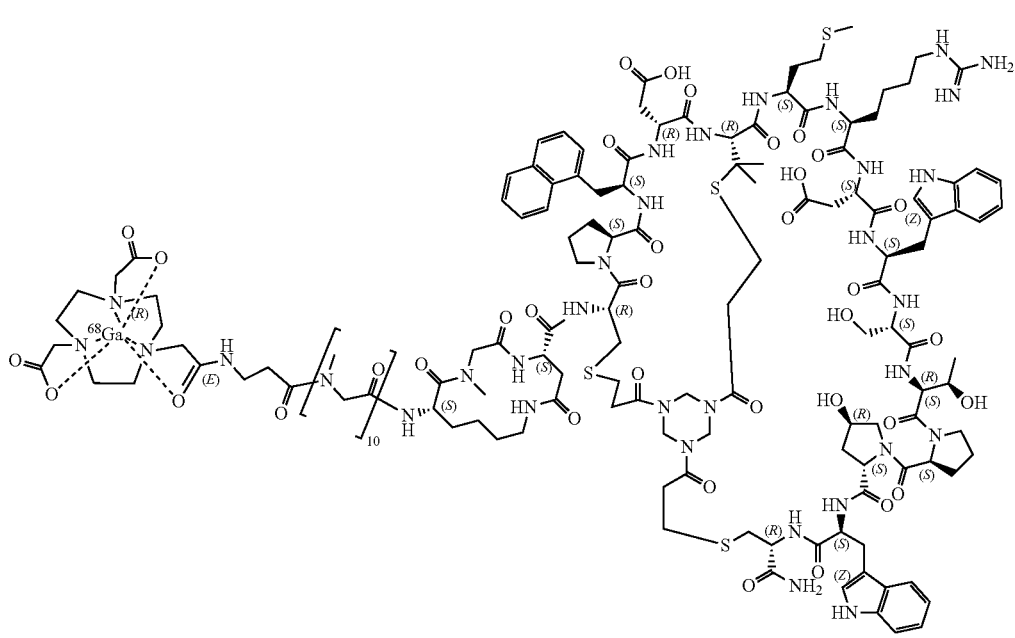

Synthetic route

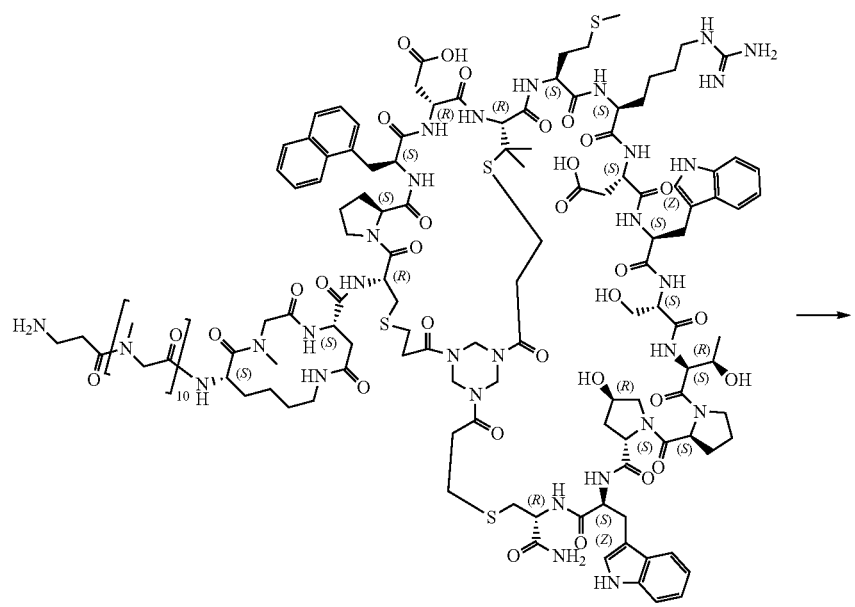

-continued

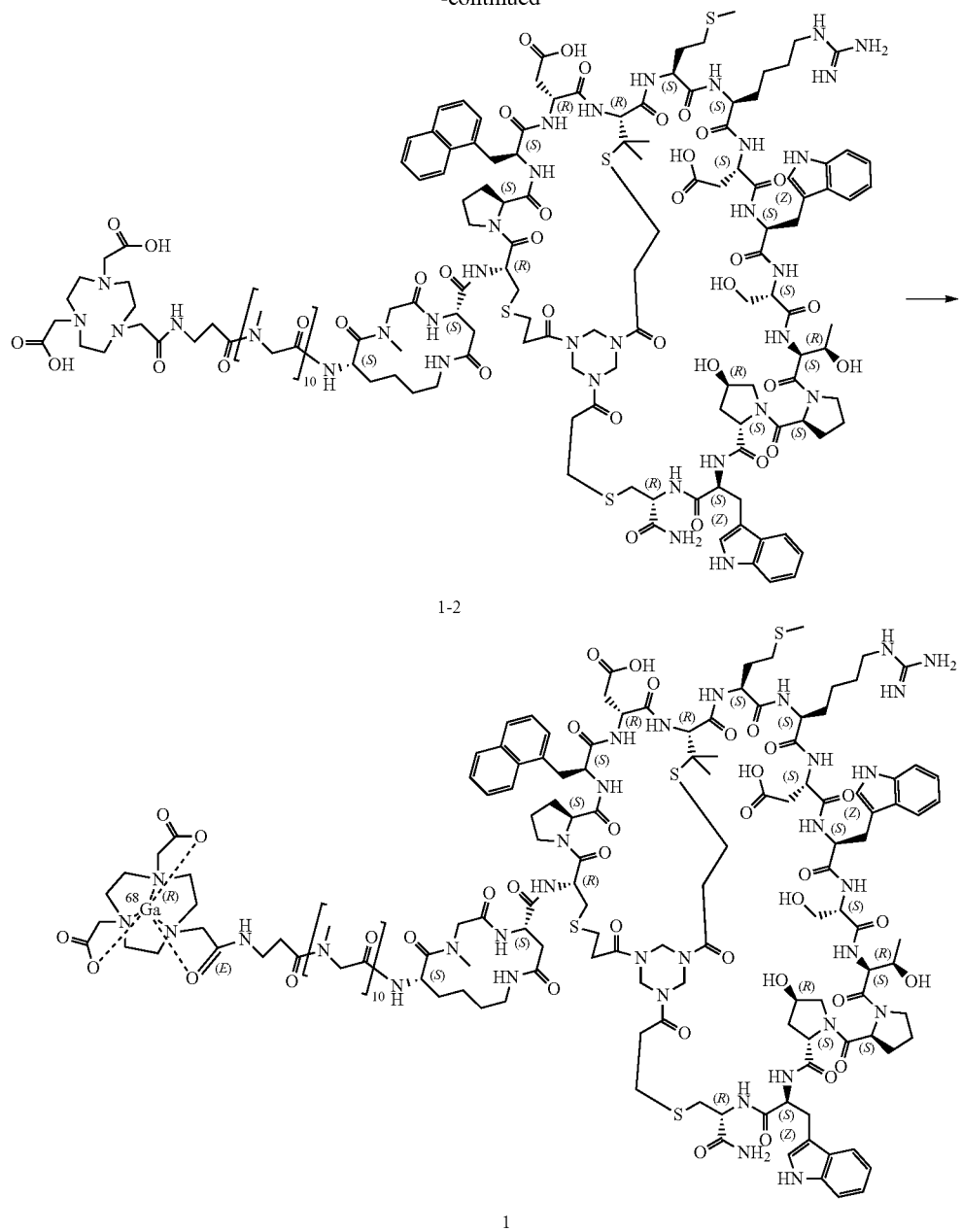

1-2

1

Step 1: Synthesis of Compound 1-1

Reference is made to the synthesis of WO 2023/051396 A1 Pepitide_2

Step 2: Synthesis of Compound 1-2

Compound 1-1 (10 mg) was dissolved in N,N-dimethylformamide (1 mL), 1,4-diacetic acid-1,4,7-triazacyclononane-7-acetic acid-N-hydroxysuccinimide ester (5 mg) was added, then N,N-diisopropylethyl amine was added to adjust pH to 8.5, shaken at room temperature overnight, separated and purified by HPLC [column type (Hypersil Gold C18 10×250 mm), (mobile phase A: 20 mmol/L potassium dihydrogen phosphate aqueous solution, mobile phase B: acetonitrile), flow rate (3 mL/min), gradient (B: 0-10 min 20% to 33%, 10-40 min 33% to 43%, 40-50 min 43% to 53%, 50-52 min keep at 53%, 52-52.5 min 53% to 20%, 52.5-60 min keep at 20%)], the fractions with the major peak as the target product were collected and lyophilized to obtained compound 1-2.

MS 1782.79944 (M/z=[M+2H$^+$]$^{2+}$/2).

Step 3: Synthesis of Compound 1

Activation of C18 cartridge: the mixture was rinsed with ethanol (10 mL), blown dry with air, then rinsed with sterile water for injection (10 mL), blown dry with air for later use.

Preparation of $^{68}$Ga eluent: the Ge-68/Ga-68 generator was rinsed with dilute hydrochloric acid (0.05 M, 4 mL) to obtain a hydrochloric acid eluent of $^{68}$Ga. Compound 1-2 (0.5 mg) was dissolved in purified water (100 μL). 20 μL of this was added to a 6 mL cryovial and then dissolved in sodium acetate solution (0.25 M, 1 mL) followed by adding the $^{68}$Ga hydrochloric acid eluent (4 mL, 47.3 mCi). Shake the mixture well and react with shaking at 100° C. for 15 min and cool to room temperature. After diluting with purified water (10 mL), the reaction solution was slowly injected into an activated Sep-Pak C18 column, rinsed with 10 mL of purified water to remove unreacted gallium ions, blown dry, and the target substance was rinsed with ethanol (0.8 mL). The eluent was concentrated to less than 0.2 mL by using with a nitrogen evaporator at 65° C., diluted with normal saline to 2 mL, and placed in a lead tank for later use.

Example 2

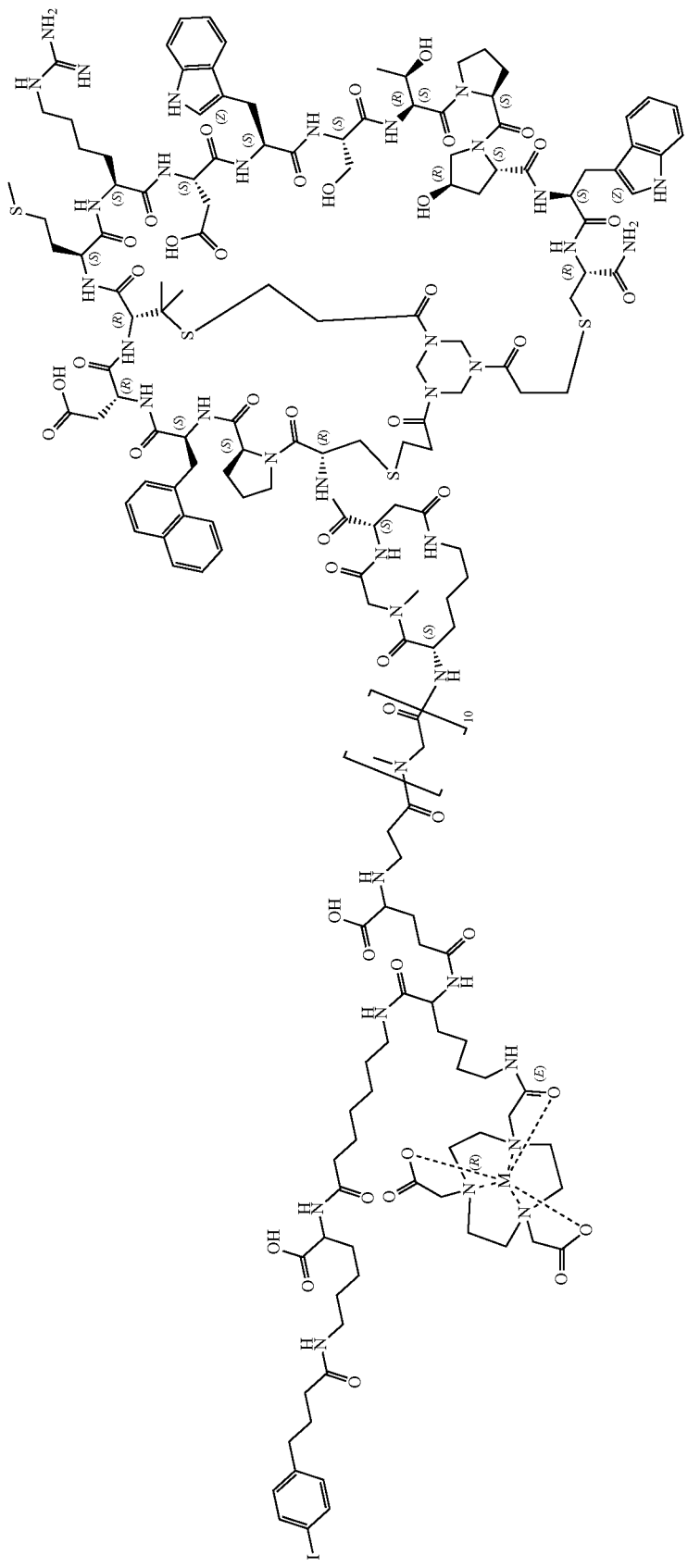

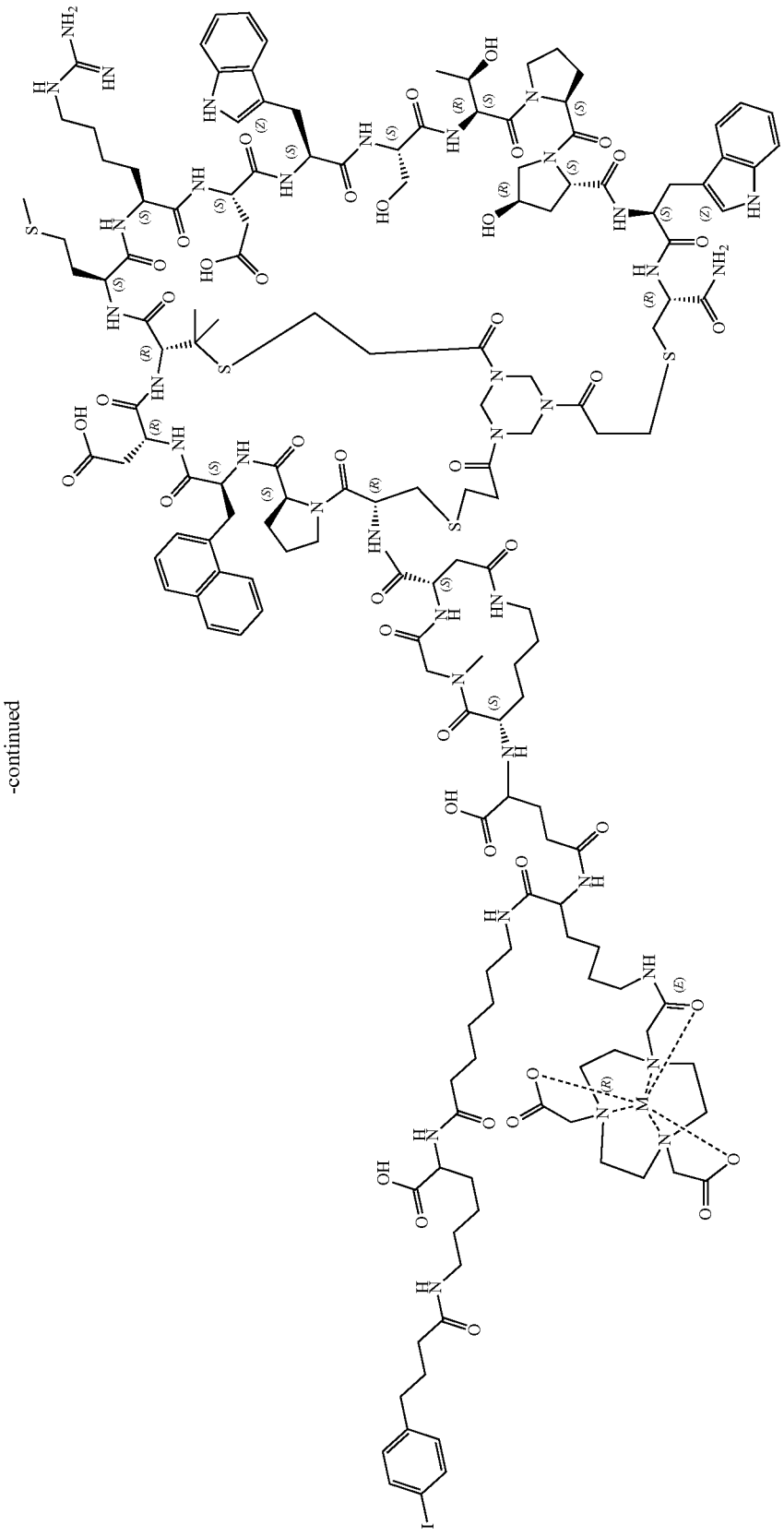

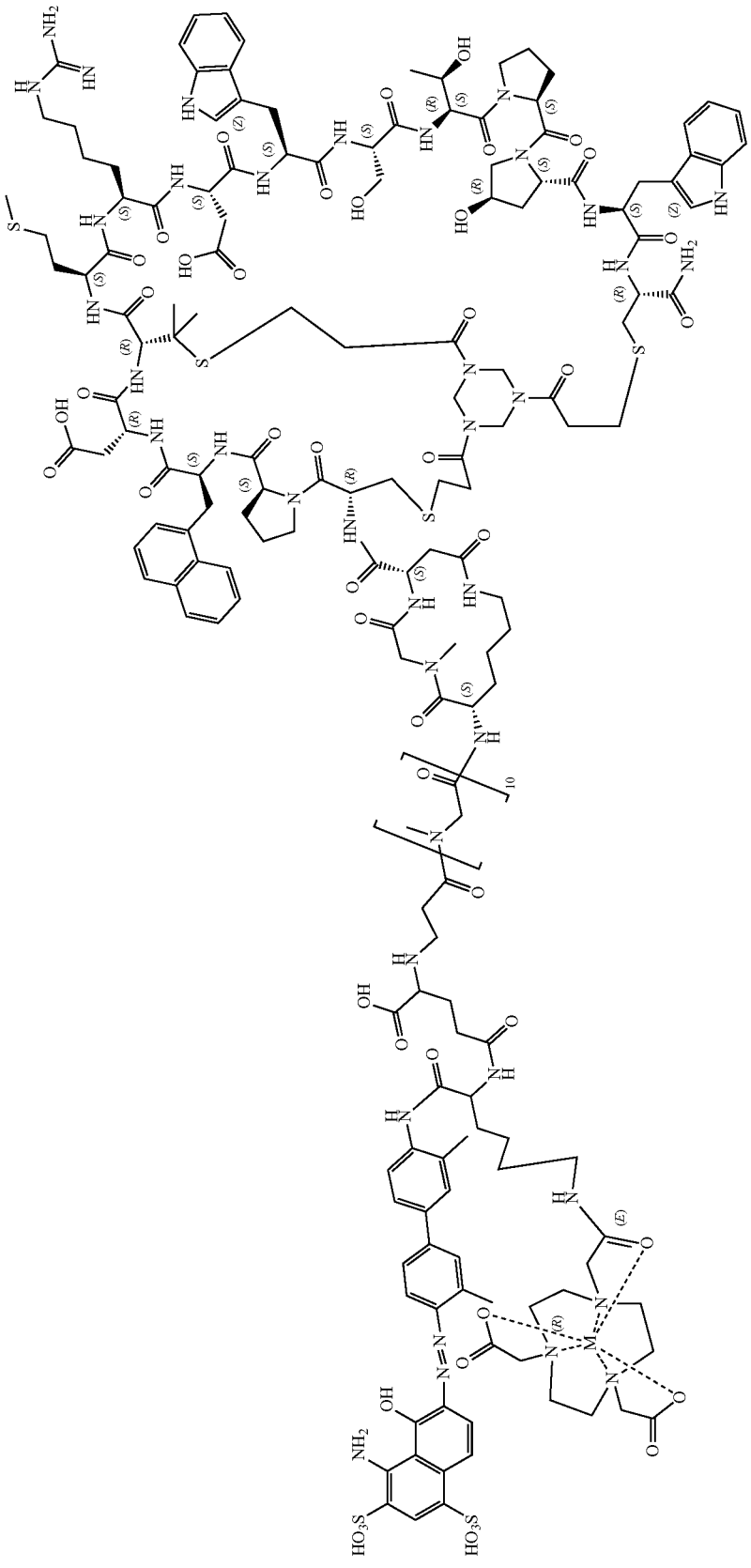

-continued
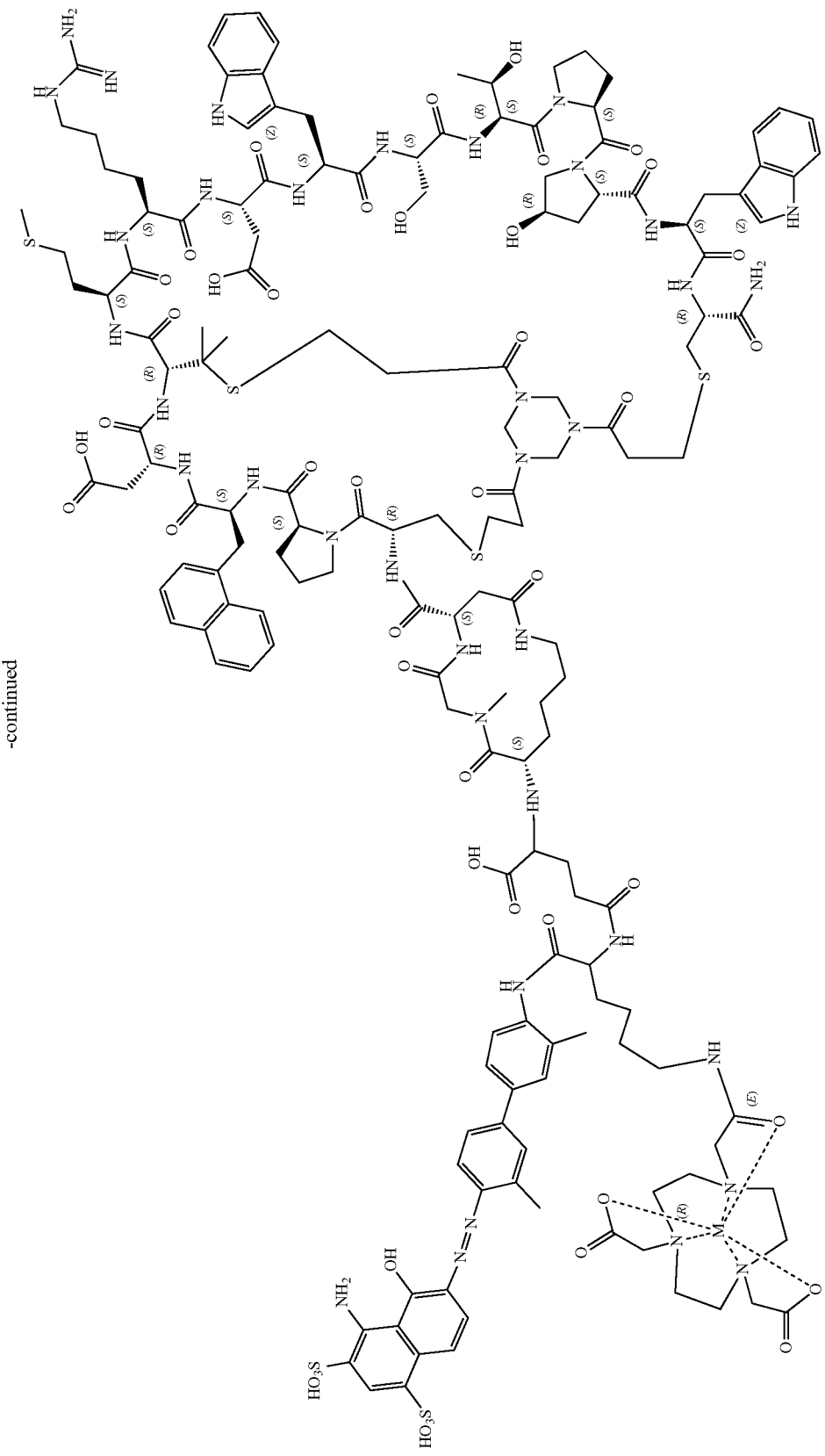

wherein M represents $^{131}$I, $^{125}$I, $^{111}$In, $^{177}$Lu, $^{68}$Ga, $^{99}$TC, $^{153}$Sm, $^{89}$Sr, $^{223}$Ra, $^{188}$Re, $^{90}$Y, $^{18}$F, $^{89}$Zr, $^{64}$Cu, $^{225}$Ac, $^{223}$Ra, $^{213}$Bi, $^{211}$At, $^{188}$Re, $^{77}$Br, $^{212}$Pb.
Example 3
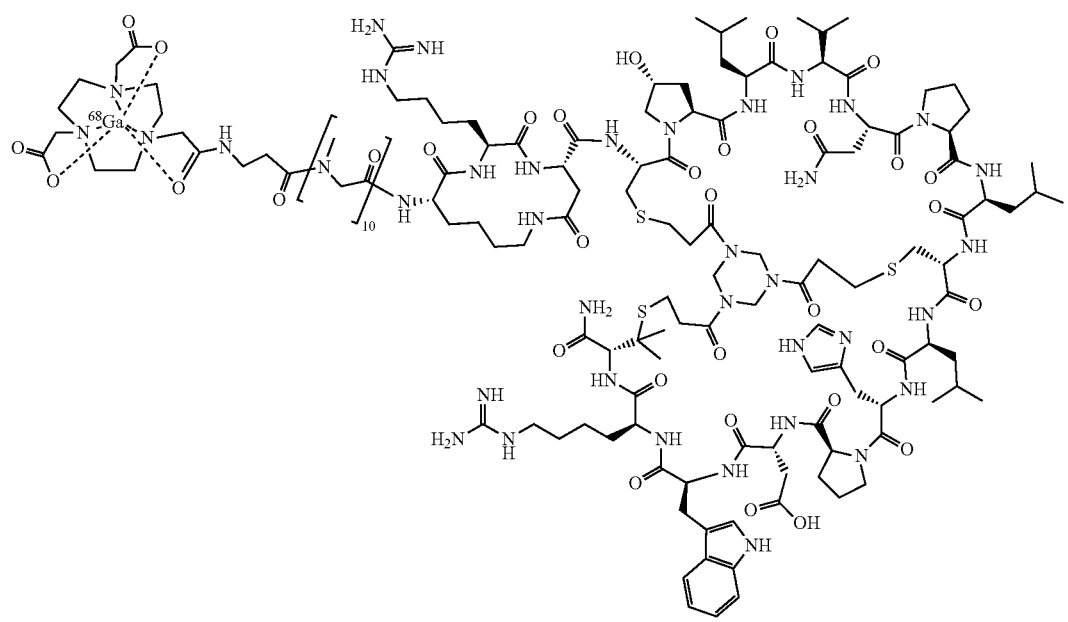
1
Synthetic route
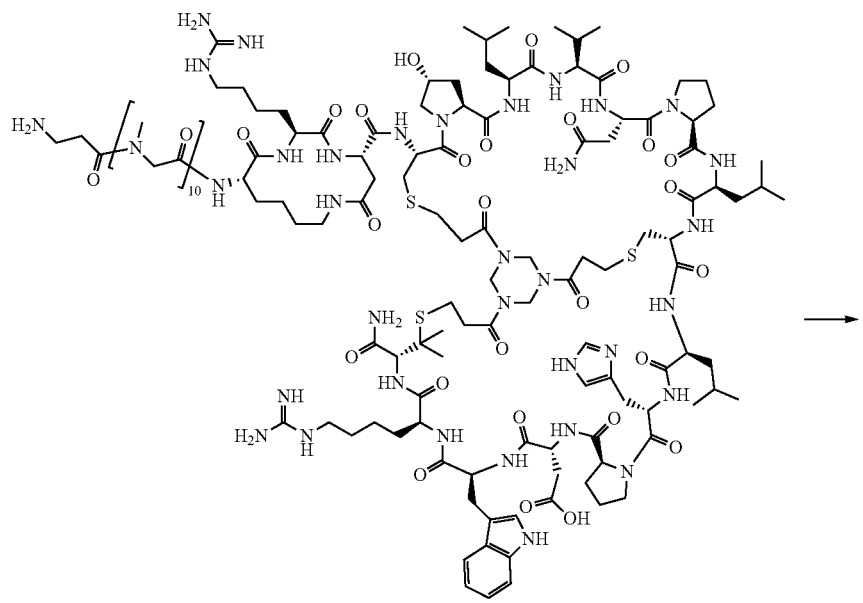
1-1

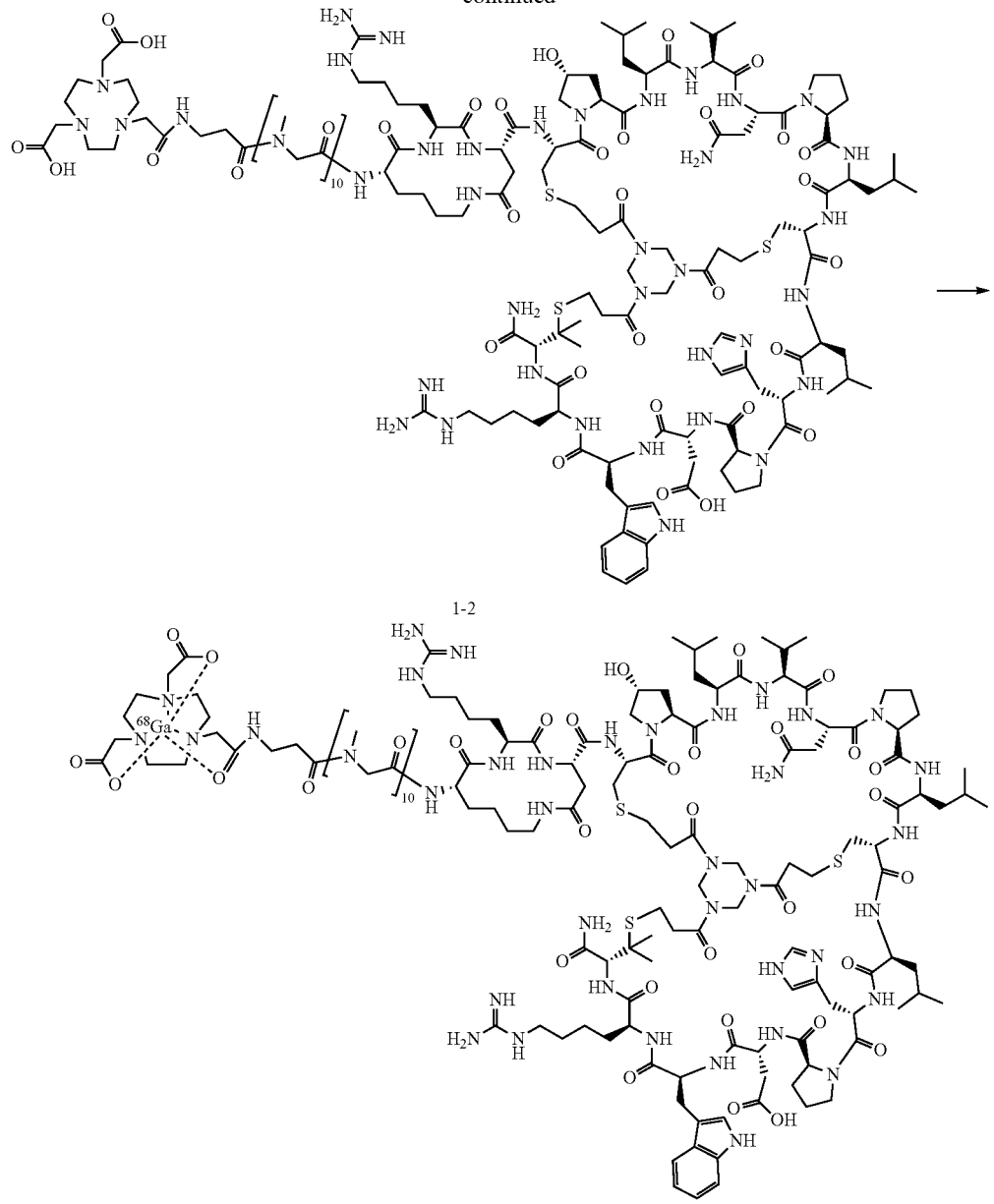

Step 1: Synthesis of Compound 1-1

Reference is made to WO 2023/020485 A1 for the synthesis of PDC_8.

Step 2: Synthesis of Compound 1-2

Compound 1-1 (10 mg) was dissolved in N,N-dimethylformamide (1 mL), 1,4-diacetic acid-1,4,7-triazacyclononane-7-acetic acid-N-hydroxysuccinimide ester (NOTA-NHS ester) (5 mg) was added, then N,N-diisopropylethyl amine was added to adjust pH to 8.0, shaken at room temperature overnight, separated and purified by HPLC [column type (Hypersil Gold C18 10×250 mm), mobile phase (A: 0.1% trifluoroacetic acid in water, mobile phase B: 0.1% trifluoroacetic acid in acetonitrile), flow rate (3 mL/min), gradient (B: 0-10 min 20% to 33%, 10-20 min 33% to 37%, 20-22 min 37% to 20%, 22-25 min keep at 20%)], the fractions with the major peak as the target product were collected and lyophilized to obtained compound 1-2. Molecular Weight: 3535.1, MS+1 (measured) 884.1984 (M/z=[M+4H+]$^{4+}$/4).

Step 3: Synthesis of Compound 1

Activation of C18 cartridge: the mixture was rinsed with ethanol (10 mL), blown dry with air, then rinsed with sterile water for injection (10 mL), blown dry with air for later use.

Preparation of $^{68}$Ga eluent: the Ge-68/Ga-68 generator was rinsed with dilute hydrochloric acid (0.05 M, 4 mL), discard the first 1 mL of the eluent, and take the last 3 mL of the eluent to obtain the hydrochloric acid eluent of $^{68}$Ga.

Compound 1-2 (0.2 mg) was dissolved in purified water (200 μL). 40 μL of this was added to a 6 mL cryovial and then dissolved in sodium acetate solution (0.35 M, 0.75 mL) followed by adding the $^{68}$Ga hydrochloric acid eluent (3 mL, 41.3 mCi). Shake the mixture well and react with shaking at 50° C. for 15 min and cool to room temperature. After diluting with purified water (10 mL), the reaction solution was slowly injected into an activated Sep-Pak C18 column, rinsed with 10 mL of purified water to remove unreacted gallium ions, blown dry, and the target substance was rinsed with ethanol (2 mL). The eluent was concentrated to less than 0.1 mL with a nitrogen evaporator at 80° C., diluted with normal saline to 2 mL, and placed in a lead tank for later use.

Example 4

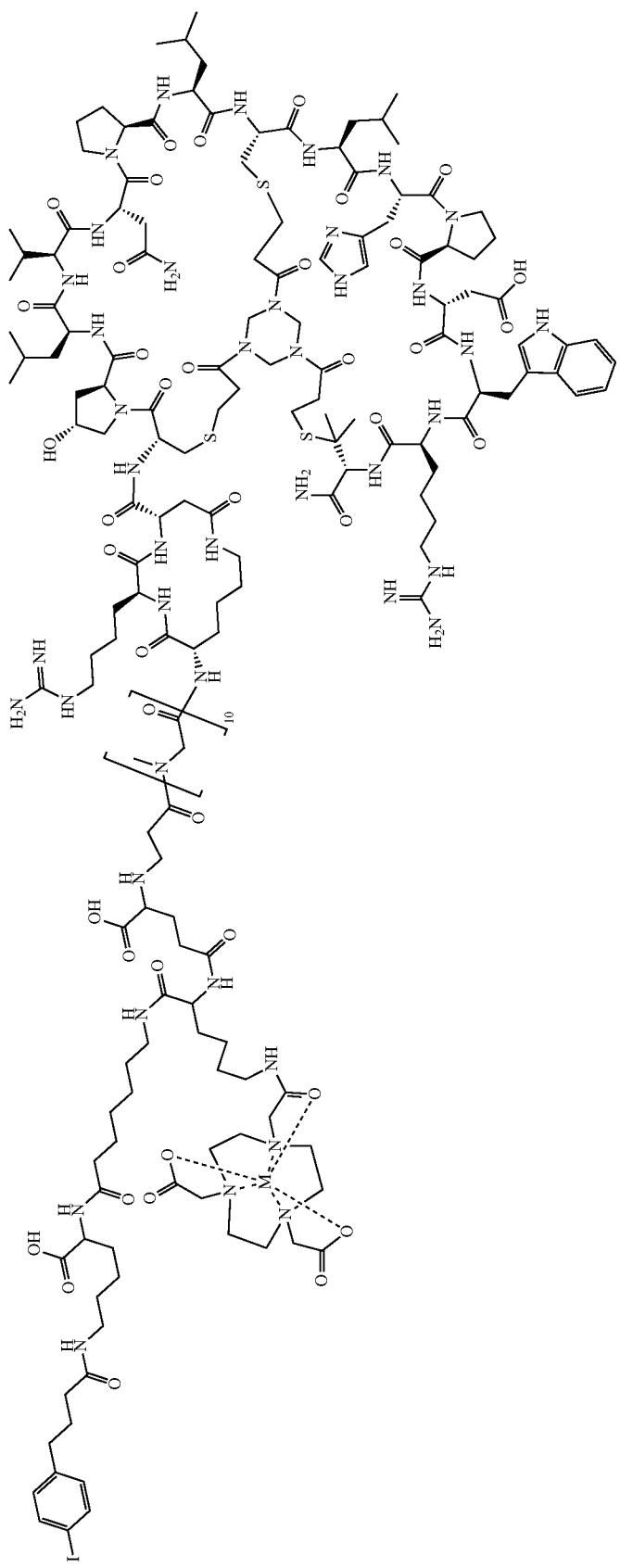

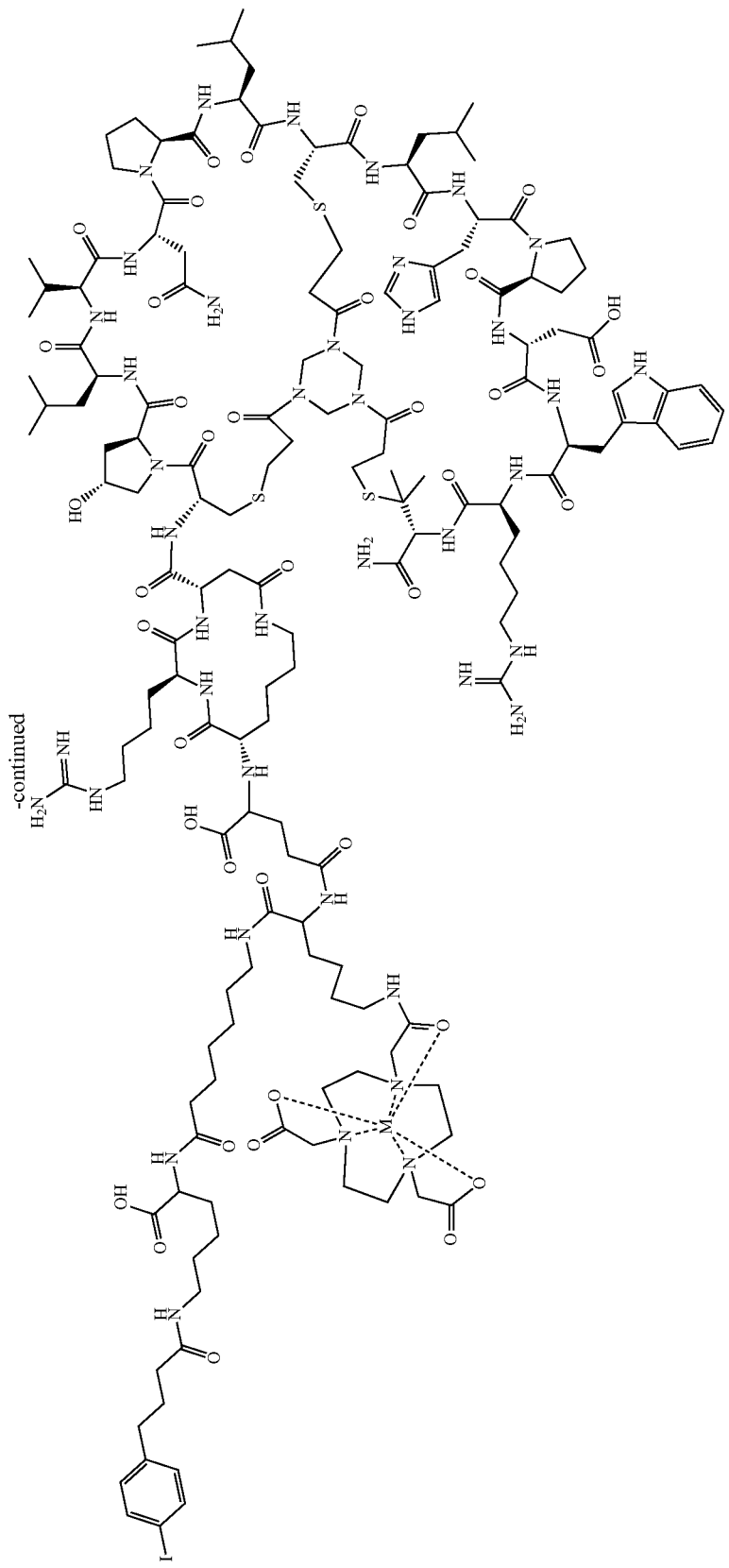

-continued
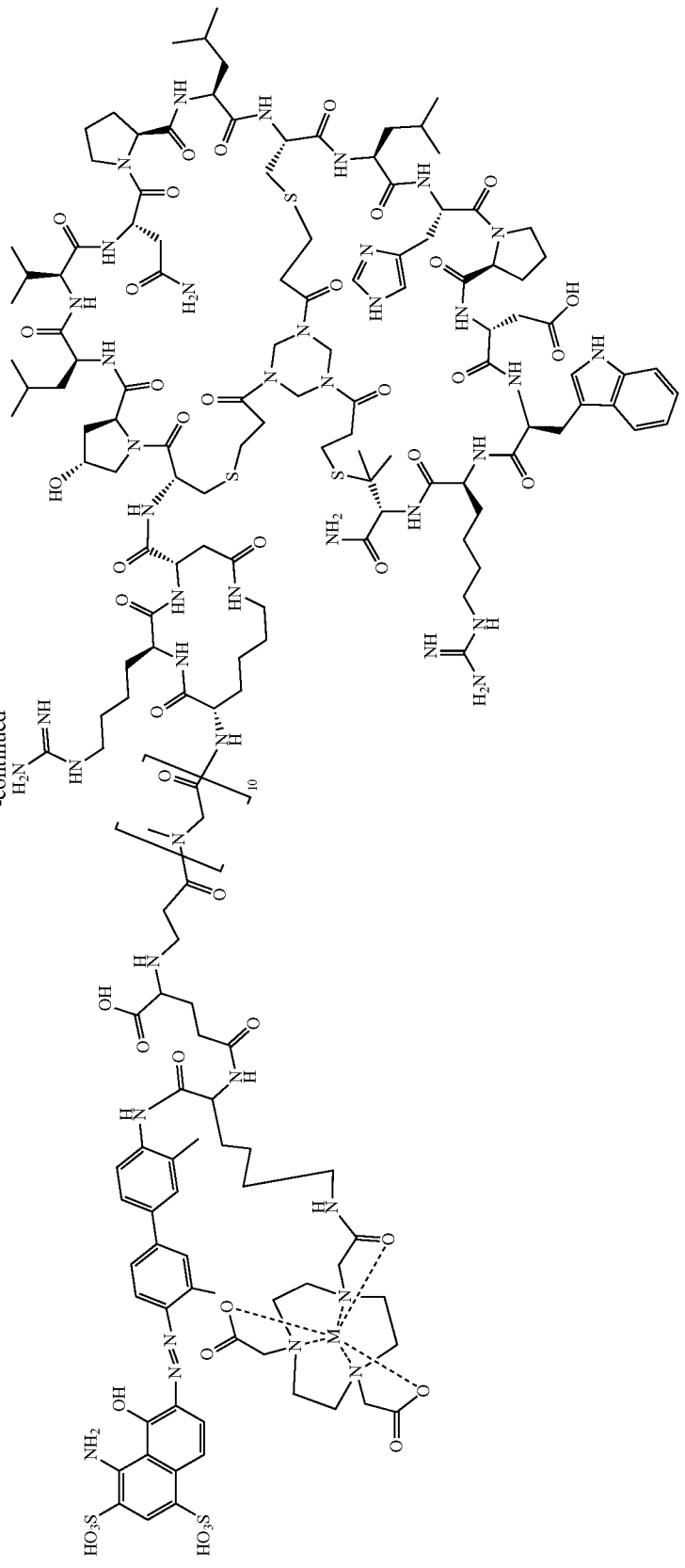

-continued
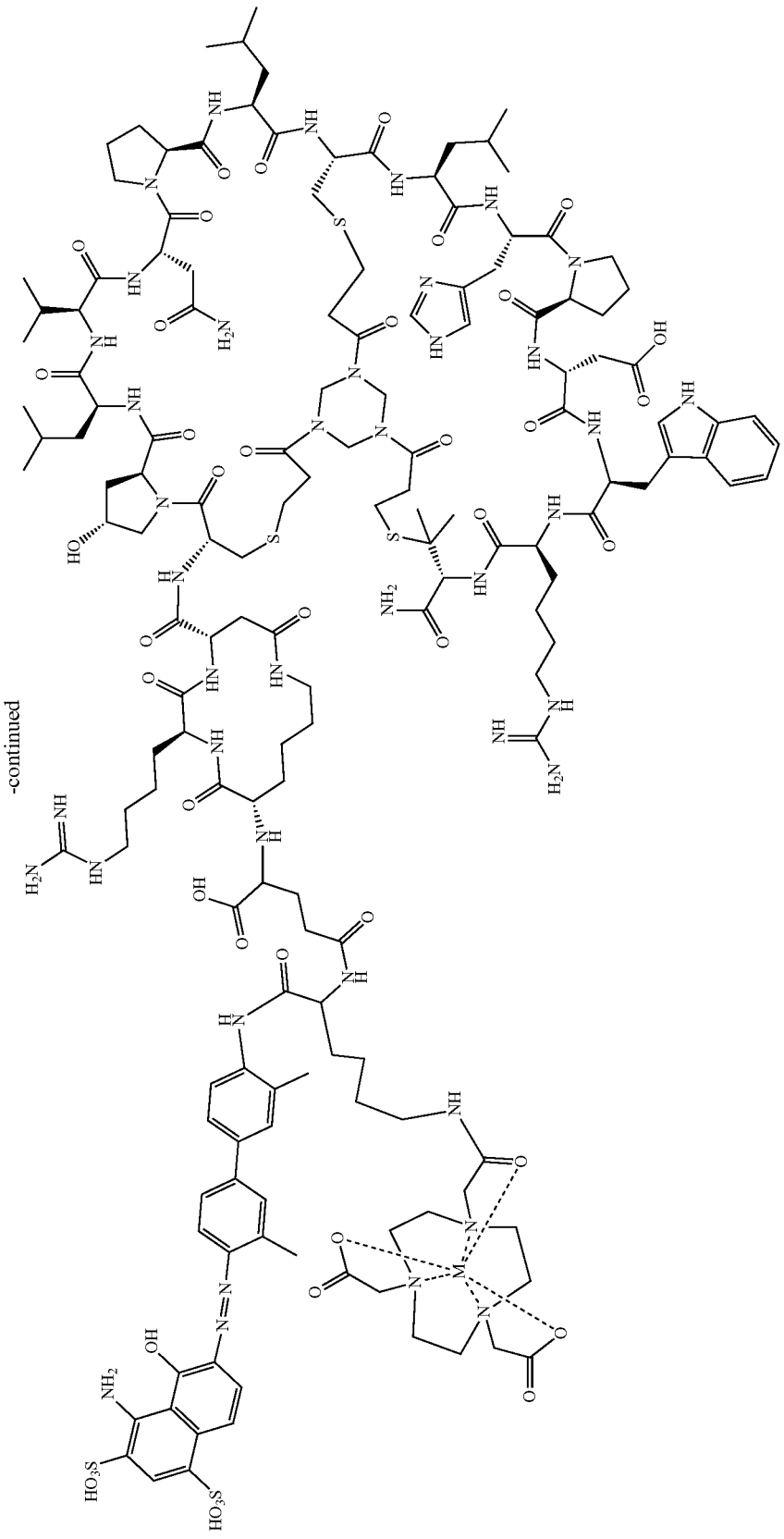

wherein M represents $^{131}$I, $^{125}$I, $^{111}$In, $^{177}$Lu, $^{68}$Ga, $^{99}$TC, $^{153}$Sm, $^{89}$Sr, $^{223}$Ra, $^{188}$Re, $^{90}$Y, $^{18}$F, $^{89}$Zr, $^{64}$Cu, $^{225}$Ac, $^{223}$Ra, $^{213}$Bi, $^{211}$At, $^{188}$Re, $^{77}$Br, $^{212}$Pb.

Experimental Example 1: Tissue Distribution Experiment of Compounds in NCI-H292 Tumor-Bearing Mice The tissue distribution characteristics of the compounds in NCI-H292 tumor-bearing mice were studied by using the NCI-H292 tumor-bearing mice model, small animal PET/CT scans were performed at different time points after a single intravenous administration of the compounds, tumors and other regions of interest was delineated to obtain radioactive uptake values.

NCI-H292 cells were cultured in DMEM high glucose medium containing inactivated 10% fetal bovine serum, 100 U/ml penicillin, and 100 μg/ml streptomycin at 37° C. in a 5% $CO_2$ incubator. Cells were subcultured normally, 3 times per week. Tumor cells in the logarithmic growth phase were used for in vivo tumor inoculation. NCI-H292 cells were suspended in physiological saline at a density of 5×106/ml, and a total of 10 nude mice were inoculated under the right flank at 0.1 ml per inoculation point. Imaging and biodistribution experiments were performed when tumors grew to approximately 300-600 mm3 (tumor volume measurement method: the long diameter and short diameter of the tumor were measured, and its volume calculation formula was: Volume=0.5× major diameter× minor diameter 2). The drug was distributed according to the animal dose on the drug distribution table, and a certain volume of compound diluent was absorbed by a 1 mL syringe, and the initial radioactive dose and initial dosimetry time were recorded. The injection time, residual radioactivity dose, and residual dose determination time were recorded after tail vein injection in tumor-bearing mice. The dose of each mouse was about 11.1 MBq. PET/CT scans of animals were performed at different time points after administration. During the scanning process, the animals continued to inhale 1-2% isoflurane to maintain the anesthetic effect, and the scanning time was recorded. In the process of experimental operation, all the above scanning time points were consistent with the theoretical time in principle. After the completion of PET/CT scanning, the images were reconstructed and the images and data were processed with the software of the device. The tumor, heart (including contents), kidney, intestine, and muscle were delineated as regions of interest. The percentage injection dose rate per gram of tissue in the area of interest (% ID/g) was obtained. The data of biological distribution was expressed as the percentage of radioactive count per gram of tissue or organ to the total dose (radioactive count) (% ID/g). Specific calculation formula:

$$\% ID/g = \frac{Counts_{organ\ or\ tissue}}{Counts_{total\ dose\ administered} \times W_{organ\ or\ tissue}} \times 100\%$$

Data for each sampling point were expressed as the mean±standard deviation (mean±SD) of 3 tumor-bearing mice.

Referring to the method of Experimental Example 1, the tissue distribution of the compound of Example 1 in the tumor-bearing mice was examined as follows:

TABLE 1

NCI-H292 tumor-bearing mice were administered a single intravenous injection of 11.1 MBq (300 μCi/mouse) of the compound in example 1. And the radioactive substance uptake values of each organ was dynamically scanned by PET/CT (% ID/g, mean ± SD value, n = 3) in 30 min.

| Injection time (min) | Heart (including contents) | Liver | Kidney | Muscle | Brain | Small intestine | Tumor |
|---|---|---|---|---|---|---|---|
| 5 | 2.15 ± 0.29 | 1.75 ± 0.5 | 8.57 ± 1.59 | 0.8 ± 0.03 | 0.69 ± 0.05 | 1.02 ± 0.13 | 2.5 ± 0.44 |
| 8 | 1.68 ± 0.2 | 1.37 ± 0.36 | 7.21 ± 1.4 | 0.7 ± 0.03 | 0.58 ± 0.04 | 0.82 ± 0.08 | 2.49 ± 0.49 |
| 11 | 1.36 ± 0.16 | 1.12 ± 0.31 | 5.62 ± 0.65 | 0.63 ± 0.06 | 0.49 ± 0.04 | 0.67 ± 0.1 | 2.45 ± 0.51 |
| 14 | 1.13 ± 0.13 | 0.92 ± 0.23 | 4.85 ± 0.61 | 0.56 ± 0.05 | 0.44 ± 0.04 | 0.59 ± 0.08 | 2.42 ± 0.51 |
| 17 | 0.97 ± 0.11 | 0.81 ± 0.21 | 4.28 ± 0.23 | 0.48 ± 0.03 | 0.38 ± 0.04 | 0.54 ± 0.11 | 2.4 ± 0.54 |
| 20 | 0.85 ± 0.1 | 0.7 ± 0.18 | 3.97 ± 0.22 | 0.45 ± 0.06 | 0.34 ± 0.04 | 0.5 ± 0.11 | 2.35 ± 0.5 |
| 23 | 0.73 ± 0.11 | 0.62 ± 0.15 | 3.69 ± 0.07 | 0.4 ± 0.05 | 0.3 ± 0.04 | 0.46 ± 0.1 | 2.29 ± 0.54 |
| 26 | 0.66 ± 0.08 | 0.55 ± 0.11 | 3.64 ± 0.18 | 0.37 ± 0.04 | 0.28 ± 0.05 | 0.42 ± 0.08 | 2.25 ± 0.57 |
| 29 | 0.59 ± 0.09 | 0.5 ± 0.13 | 3.37 ± 0.12 | 0.36 ± 0.04 | 0.25 ± 0.04 | 0.4 ± 0.08 | 2.19 ± 0.54 |
| 32 | 0.52 ± 0.08 | 0.45 ± 0.11 | 3.32 ± 0.14 | 0.34 ± 0.04 | 0.23 ± 0.04 | 0.37 ± 0.08 | 2.15 ± 0.56 |

TABLE 2

After a single intravenous administration of the compound of Example 1 of 11.1 MBq (300 μCi/mouse) in NCI-H292 tumor-bearing mice, the radioactive substance uptake values of each region of interest at different imaging time points (% ID/g, mean ± SD value, n = 3).

| Tissue | 0.5 h | 1 h | 2 h | 4 h |
|---|---|---|---|---|
| Heart (including contents) | 0.52 ± 0.08 | 0.24 ± 0.06 | 0.13 ± 0.01 | 0.11 ± 0.01 |
| Liver | 0.43 ± 0.09 | 0.21 ± 0.05 | 0.14 ± 0.01 | 0.11 ± 0.01 |
| Kidney | 3.31 ± 0.12 | 2.70 ± 0.13 | 2.57 ± 0.14 | 2.38 ± 0.21 |
| Muscle | 0.29 ± 0.02 | 0.15 ± 0.07 | 0.09 ± 0.02 | 0.09 ± 0.03 |
| Brain | 0.21 ± 0.04 | 0.10 ± 0.03 | 0.07 ± 0.02 | 0.06 ± 0.02 |
| Small intestine | 0.37 ± 0.08 | 0.30 ± 0.09 | 0.22 ± 0.07 | 0.13 ± 0.07 |
| Tumor | 2.10 ± 0.51 | 1.88 ± 0.55 | 1.68 ± 0.45 | 1.48 ± 0.35 |
| Tumor/heart | 4.03 ± 0.48 | 7.83 ± 0.50 | 13.65 ± 4.47 | 14.57 ± 5.29 |
| Tumor/liver | 4.94 ± 0.51 | 9.01 ± 0.71 | 11.90 ± 3.11 | 13.43 ± 3.91 |
| Tumor/kidney | 0.64 ± 0.17 | 0.70 ± 0.24 | 0.66 ± 0.22 | 0.63 ± 0.21 |
| Tumor/muscle | 7.20 ± 1.48 | 13.85 ± 3.41 | 17.99 ± 1.94 | 17.06 ± 2.23 |
| Tumor/brain | 10.25 ± 1.11 | 18.37 ± 1.60 | 23.02 ± 0.48 | 25.69 ± 0.84 |
| Tumor/intestine | 5.64 ± 0.17 | 6.59 ± 2.13 | 8.17 ± 2.92 | 14.00 ± 8.14 |

Experimental Example 2: In Vivo Radioactive Biological Distribution Assay of Compounds in NCI-11292 Tumor-Bearing Mice In vivo radioactive biological distribution assay: mice in the PET/CT imaging group were sacrificed immediately after the end of 4 h imaging, and mice in the inhibition group were sacrificed after 1 h imaging. Tissue samples of tumor, blood, heart, lung, liver, spleen, kidney, stomach, intestine, bone, muscle, and brain were collected by dissection, weighed and their radioactive counts were recorded. The probe uptake value in each tissue and organ of each experimental animal is expressed as radioactivity per gram of tissue as a percentage of the dose administered (% ID/g).

TABLE 3

4 h after a single intravenous administration of the injection of the compound in Example 1 of 11.1 MBq (300 μCi/mouse) to NCI-H292 tumor-bearing mice, the radioactive substance uptake values of in vitro tissue of each mouse (% ID/g).

| Viscera | S1 | S2 | S3 | Mean ± SD |
|---|---|---|---|---|
| Heart | 0.12 | 0.12 | 0.19 | 0.14 ± 0.04 |
| Liver | 0.31 | 0.25 | 0.2 | 0.25 ± 0.06 |
| Lung | 0.55 | 0.39 | 0.77 | 0.57 ± 0.19 |
| Kidney | 14.66 | 12.17 | 9.14 | 11.99 ± 2.76 |
| Spleen | 0.41 | 0.29 | 0.45 | 0.38 ± 0.08 |
| Stomach | 0.24 | 0.3 | 0.32 | 0.29 ± 0.04 |
| Bone | 0.35 | 0.34 | 0.37 | 0.35 ± 0.02 |
| Muscle | 0.1 | 0.08 | 0.14 | 0.11 ± 0.03 |
| Intestine | 0.13 | 0.11 | 0.14 | 0.13 ± 0.02 |
| Brain | 0.02 | 0.02 | 0.03 | 0.02 ± 0.01 |
| Blood | 0.22 | 0.22 | 0.41 | 0.28 ± 0.11 |
| Tumor | 4.18 | 3.00 | 5.15 | 4.11 ± 1.08 |
| Tumor/heart | 34.83 | 25.00 | 27.11 | 28.98 ± 5.18 |
| Tumor/liver | 13.48 | 12.00 | 25.75 | 17.08 ± 7.55 |
| Tumor/lung | 7.60 | 7.69 | 6.69 | 7.33 ± 0.55 |
| Tumor/kidney | 0.29 | 0.25 | 0.56 | 0.37 ± 0.17 |
| Tumor/spleen | 10.20 | 10.34 | 11.44 | 10.66 ± 0.68 |
| Tumor/stomach | 17.42 | 10.00 | 16.09 | 14.5 ± 3.96 |
| Tumor/bone | 11.94 | 8.82 | 13.92 | 11.56 ± 2.57 |
| Tumor/muscle | 41.80 | 37.50 | 36.79 | 38.7 ± 2.71 |
| Tumor/intestine | 32.15 | 27.27 | 36.79 | 32.07 ± 4.76 |
| Tumor/brain | 209.00 | 150.00 | 171.67 | 176.89 ± 29.84 |
| Tumor/blood | 19.00 | 13.64 | 12.56 | 15.07 ± 3.45 |

Experimental Example 3: Tissue Distribution Assay of Compounds in PC-3 Tumor-Bearing Mice The tissue distribution characteristics of the compounds in PC-3 tumor-bearing mice were studied by using the PC-3 tumor-bearing mice model, small animal PET/CT scans were performed at different time points after a single intravenous administration of the compounds, tumors and other regions of interest were delineated to obtain radioactive uptake values.

In vitro culture of human prostate cancer PC-3 cells: PC-3 cells were cultured in Ham's F-12k medium containing inactivated 10% fetal bovine serum, 100 U/mL penicillin, and 100 μg/mL streptomycin at 37° C. in a 5% $CO_2$ incubator. Cells were subcultured normally, 3 times per week. Tumor cells in the logarithmic growth phase were used for in vivo tumor inoculation. PC-3 cells were suspended in saline at a density of 5×106/mL, and a total of 15 nude mice were inoculated under the right flank at 0.1 mL per inoculation point. Imaging and biodistribution experiments were performed when tumors grew to 300-600 $mm^3$ (tumor volume measurement method: the long diameter and short diameter of the tumor were measured, and its volume calculation formula was: volume=0.5× major diameter× minor $diameter^2$). The drug was distributed according to the animal dose on the drug distribution table, and a certain volume of compound diluent was absorbed by a 1 mL insulin syringe, and the initial radioactive dose and initial dosimetry time were recorded. The injection time, residual radioactivity dose, and residual dose determination time were recorded after tail vein injection in tumor-bearing mice. The dose of each mouse was about 11.1 MBq. PET/CT scans of animals were performed at different time points after administration. During the scanning process, the animals continued to inhale 1-2% isoflurane to maintain the anesthetic effect, and the scanning time was recorded. In the process of experimental operation, all the above scanning time points were consistent with the theoretical time in principle. After the completion of PET/CT scanning, the images were reconstructed and the images and data were processed with the software of the device. The tumor, heart (including contents), kidney, intestine, and muscle were delineated as regions of interest. The percentage injection dose rate per gram of tissue in the area of interest (% ID/g) was obtained. The data of biological distribution was expressed as the percentage of radioactive count per gram of tissue or organ to the total dose (radioactive count) (% ID/g). Specific calculation formula:

$$\% ID/g = \frac{Counts_{organ\ or\ tissue}}{Counts_{total\ dose\ administered} \times W_{organ\ or\ tissue}} \times 100\%$$

Data for each sampling point were expressed as the mean standard deviation (mean SD) of 3 tumor-bearing mice.

Referring to the method of Experimental Example 3, the tissue distribution of the compound of example 3 in the tumor-bearing mice was examined as follows:

TABLE 4

30 min after a single intravenous administration of the injection of the compound in example 3 of 11.1 MBq (300 μCi/mouse) to PC-3 tumor-bearing mice, the radioactive substance uptake values of each organ dynamically scanned by PET/CT (% ID/g, mean ± SD value, n = 3).

| Post-injection collection time (min) | Heart (including contents) | Liver | Kidney | Muscle | Tumor |
|---|---|---|---|---|---|
| 2 | 3.35 ± 0.35 | 2.62 ± 0.25 | 14.99 ± 0.64 | 1.06 ± 0.10 | 1.37 ± 0.21 |
| 5 | 2.95 ± 0.63 | 2.22 ± 0.41 | 14.63 ± 2.02 | 1.02 ± 0.18 | 1.41 ± 0.13 |
| 8 | 2.59 ± 0.67 | 1.94 ± 0.35 | 14.94 ± 2.94 | 0.97 ± 0.16 | 1.45 ± 0.13 |
| 11 | 2.18 ± 0.51 | 1.60 ± 0.23 | 15.19 ± 2.41 | 0.91 ± 0.19 | 1.46 ± 0.09 |
| 14 | 1.86 ± 0.41 | 1.44 ± 0.23 | 15.08 ± 2.42 | 0.82 ± 0.12 | 1.46 ± 0.07 |
| 17 | 1.65 ± 0.38 | 1.23 ± 0.15 | 14.40 ± 2.34 | 0.74 ± 0.13 | 1.48 ± 0.08 |
| 20 | 1.51 ± 0.36 | 1.14 ± 0.14 | 14.41 ± 2.61 | 0.69 ± 0.11 | 1.51 ± 0.13 |
| 23 | 1.41 ± 0.31 | 1.07 ± 0.14 | 13.92 ± 2.02 | 0.66 ± 0.14 | 1.46 ± 0.09 |
| 26 | 1.28 ± 0.30 | 0.97 ± 0.16 | 12.54 ± 1.35 | 0.67 ± 0.16 | 1.46 ± 0.13 |
| 29 | 1.18 ± 0.24 | 0.91 ± 0.10 | 11.51 ± 0.94 | 0.56 ± 0.11 | 1.45 ± 0.14 |

TABLE 5

After a single intravenous administration of the compound of example 3 of 11.1 MBq (300 μCi/mouse) in PC-3 tumor-bearing mice, the radioactive substance uptake values of each region of interest at different imaging time points (% ID/g, mean ± SD value, n = 3).

| Tissue | 0.5 h | 1 h | 2 h | 4 h |
|---|---|---|---|---|
| Heart (including contents) | 1.21 ± 0.30 | 0.65 ± 0.25 | 0.15 ± 0.06 | 0.06 ± 0.02 |
| Liver | 0.92 ± 0.07 | 0.59 ± 0.21 | 0.22 ± 0.04 | 0.13 ± 0.05 |
| Kidney | 11.55 ± 1.26 | 9.68 ± 0.18 | 8.82 ± 0.68 | 8.03 ± 0.35 |
| Muscle | 0.55 ± 0.15 | 0.26 ± 0.05 | 0.07 ± 0.02 | 0.03 ± 0.01 |
| Tumor | 1.43 ± 0.13 | 1.27 ± 0.28 | 1.04 ± 0.45 | 0.98 ± 0.46 |
| Tumor/heart | 1.23 ± 0.25 | 2.08 ± 0.74 | 6.97 ± 3.01 | 15.93 ± 5.85 |
| Tumor/liver | 1.57 ± 0.14 | 2.24 ± 0.68 | 4.53 ± 1.44 | 9.72 ± 8.48 |
| Tumor/kidney | 0.12 ± 0.01 | 0.13 ± 0.03 | 0.12 ± 0.06 | 0.12 ± 0.06 |
| Tumor/muscle | 2.69 ± 0.47 | 5.01 ± 0.82 | 15.59 ± 3.52 | 31.39 ± 9.05 |

Experimental Example 4: In Vivo Radiobiological Distribution Assay of Compounds in PC-3 Tumor-Bearing Mice In vivo radiobiological distribution assay: mice in the PET/CT imaging group were sacrificed immediately after the end of 4 h imaging, and mice in the inhibition group were sacrificed after 1 h imaging. Tissue samples of tumor, blood, heart, lung, liver, spleen, kidney, stomach, intestine, bone, muscle, and brain were collected by dissection, weighed and their radioactive counts were recorded. The probe uptake value in each tissue and organ of each experimental animal is expressed as radioactivity per gram of tissue as a percentage of the dose administered (% ID/g).

TABLE 6

4 h after a single intravenous administration of the injection of the compound in example 3 of 11.1 MBq (300 μCi/mouse) to PC-3 tumor-bearing mice, the radioactive substance uptake values of in vitro tissue of each mouse (% ID/g).

| Viscera | S1 | S2 | S3 | Mean ± SD |
|---|---|---|---|---|
| Heart | 0.31 | 0.29 | 0.20 | 0.26 ± 0.06 |
| Liver | 0.66 | 0.50 | 0.71 | 0.62 ± 0.11 |
| Lung | 0.49 | 0.46 | 0.31 | 0.42 ± 0.10 |
| Kidney | 62.66 | 51.27 | 57.12 | 57.01 ± 5.70 |
| Spleen | 0.66 | 0.54 | 0.59 | 0.60 ± 0.06 |
| Stomach | 0.22 | 0.15 | 0.17 | 0.18 ± 0.04 |
| Bone | 1.15 | 1.69 | 0.84 | 1.23 ± 0.43 |
| Muscle | 0.46 | 0.76 | 0.30 | 0.50 ± 0.23 |
| Intestine | 0.42 | 0.29 | 0.22 | 0.31 ± 0.10 |
| Brain | 0.11 | 0.05 | 0.06 | 0.08 ± 0.03 |
| Blood | 0.20 | 0.56 | 0.16 | 0.31 ± 0.22 |
| Tumor | 5.03 | 2.19 | 5.90 | 4.38 ± 1.94 |
| Tumor/heart | 16.45 | 7.47 | 30.12 | 18.01 ± 11.40 |
| Tumor/liver | 7.63 | 4.34 | 8.30 | 6.76 ± 2.12 |
| Tumor/lung | 10.25 | 4.78 | 19.01 | 11.35 ± 7.18 |
| Tumor/kidney | 0.08 | 0.04 | 0.10 | 0.08 ± 0.03 |
| Tumor/spleen | 7.58 | 4.03 | 10.00 | 7.20 ± 3.00 |
| Tumor/stomach | 22.84 | 14.71 | 34.54 | 24.03 ± 9.97 |
| Tumor/bone | 4.39 | 1.30 | 7.02 | 4.23 ± 2.87 |
| Tumor/muscle | 11.01 | 2.89 | 19.97 | 11.29 ± 8.54 |
| Tumor/intestine | 12.02 | 7.64 | 27.31 | 15.66 ± 10.33 |
| Tumor/brain | 44.40 | 40.18 | 91.90 | 58.83 ± 28.72 |
| Tumor/blood | 24.89 | 3.88 | 36.90 | 21.89 ± 16.71 |

What is claimed is:

1. A radioactive drug conjugate having the following structure:

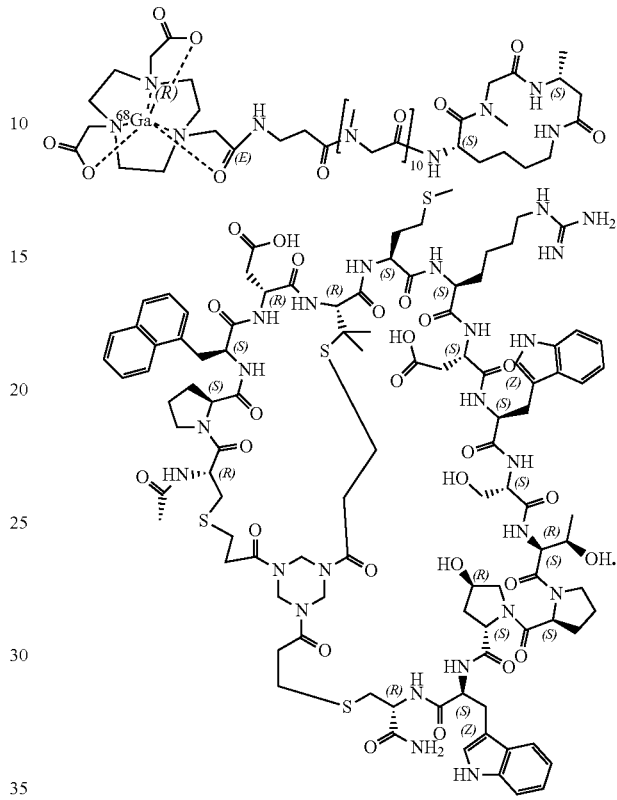

2. The radioactive drug conjugate according to claim 1, wherein the radioactive drug conjugate is a PET tracer.

3. The radioactive drug conjugate according to claim 1, wherein the radioactive drug conjugate is used for PET imaging in lung cancer detection.

* * * * *